US009056860B2

(12) United States Patent
Scott et al.

(10) Patent No.: US 9,056,860 B2
(45) Date of Patent: Jun. 16, 2015

(54) SYNTHESIS OF ANTIVIRAL COMPOUND

(71) Applicant: Gilead Pharmasset LLC, Foster City, CA (US)

(72) Inventors: Robert William Scott, San Mateo, CA (US); Justin Philip Vitale, San Mateo, CA (US); Kenneth Stanley Matthews, San Francisco, CA (US); Martin Gerald Teresk, San Jose, CA (US); Alexandra Formella, San Mateo, CA (US); Jared Wayne Evans, Belmont, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 0 days.

(21) Appl. No.: 13/800,202

(22) Filed: Mar. 13, 2013

(65) Prior Publication Data

US 2013/0324740 A1 Dec. 5, 2013

Related U.S. Application Data

(60) Provisional application No. 61/655,935, filed on Jun. 5, 2012.

(51) Int. Cl.
*C07D 403/14* (2006.01)
*C07D 403/04* (2006.01)

(52) U.S. Cl.
CPC ............ *C07D 403/14* (2013.01); *C07D 403/04* (2013.01)

(58) Field of Classification Search
USPC ........................................................ 548/300.7
See application file for complete search history.

(56) References Cited

U.S. PATENT DOCUMENTS 8,088,368 B2 1/2012 Guo et al.
8,273,341 B2 9/2012 Guo et al.
8,575,118 B2 11/2013 Guo et al.
8,669,234 B2 3/2014 Guo et al.
2011/0306541 A1 12/2011 Delaney et al.
2013/0324496 A1 12/2013 Scott et al.
2014/0039021 A1 2/2014 Bacon et al.
2014/0051656 A1 2/2014 Bacon et al.

FOREIGN PATENT DOCUMENTS

WO WO2010/132601 11/2010

OTHER PUBLICATIONS

U.S. Appl. No. 14/280,478, filed May 16, 2014, Bacon et al.
International Search Report and Written Opinion dated Aug. 16, 2013 from PCT/US2013/044148.

*Primary Examiner* — Laura L. Stockton
(74) *Attorney, Agent, or Firm* — J. Elin Hartrum; Brian C. Remy

(57) ABSTRACT

The present disclosure provides processes for the preparation of a compound of formula I:

(I)

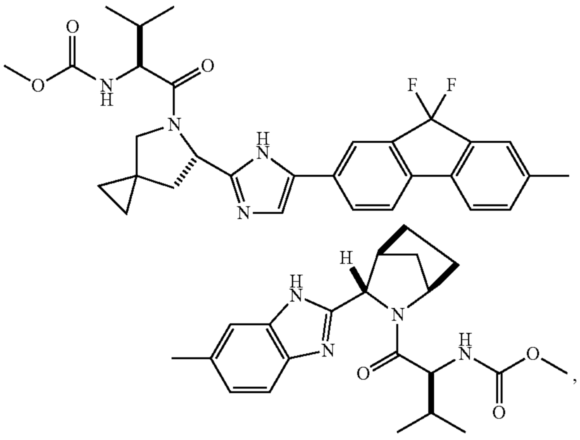

which is useful as an antiviral agent. The disclosure also provides compounds that are synthetic intermediates to compounds of formula I.

13 Claims, 2 Drawing Sheets

SYNTHESIS OF ANTIVIRAL COMPOUND

CROSS REFERENCE TO RELATED APPLICATIONS

This application claims the benefit under 35 U.S.C. §119 (e) to U.S. Provisional Application Ser. No. 61/655,935, filed on Jun. 5, 2012, the entirety of which is incorporated herein by reference.

BACKGROUND

The present disclosure relates generally to the field of organic synthetic methodology for the preparation of antiviral compounds and their synthetic intermediates.

Hepatitis C is recognized as a chronic viral disease of the liver which is characterized by liver disease. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

SUMMARY

The present disclosure provides in one embodiment a process for making a compound of formula I:

(I)

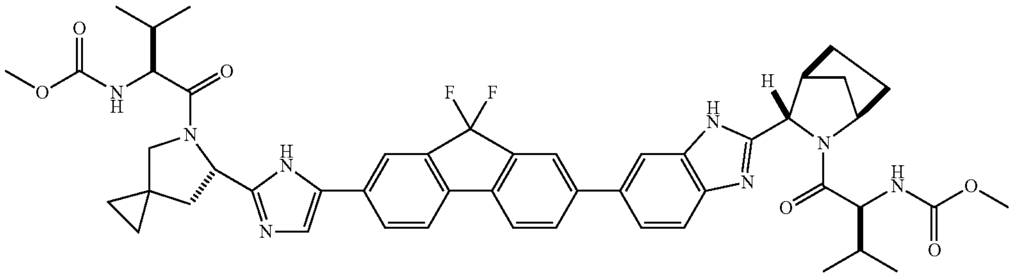

, or a pharmaceutically acceptable salt or solvate thereof. Compound of formula I, also known as ledipasvir, has the chemical name: (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester. The process comprises the following steps:

(A) coupling a compound of formula (i)

(i)

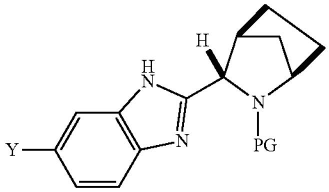

with a compound of formula (ii)

(ii)

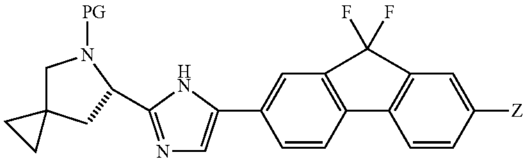

in the presence of a metal catalyst and base to yield a compound of formula (iii) or a salt thereof:

(iii)

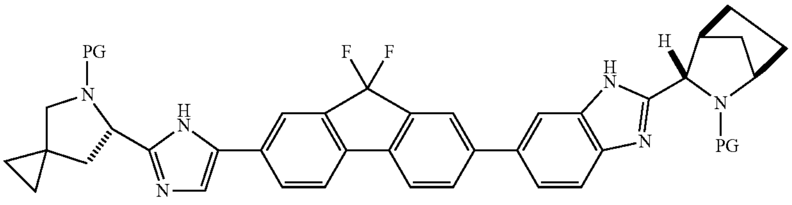

;

(B) Deprotecting a compound of formula (iii) to yield a compound of formula (iv):

(iv)

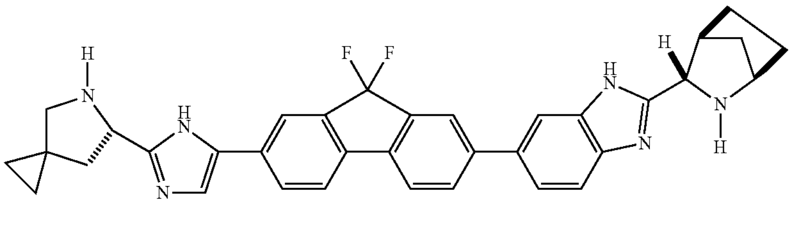

or a salt thereof; and (C) Contacting the compound of formula (iv) with (S)-2-(methoxycarbonylamino)-3-methylbutanoic acid:

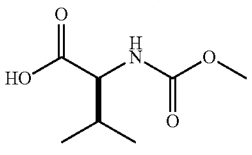

to yield a compound of formula I.

Each PG independently is an amine protecting group.

Substituents Y and Z are independently selected from Br and —B(OR)(OR'). In one embodiment, when Y is —B(OR)(OR'), then Z is Br, and in another embodiment, when Y is Br, then Z is —B(OR)(OR').

The substituents R and R' are independently selected from the group consisting of hydrogen and straight or branched $C_{1-8}$-alkyl, or R and R' together represent a straight or branched $C_{1-8}$-alkylene, $C_{3-8}$-cycloalkylene, or $C_{6-12}$-arylene.

Any alkyl, alkylene, cycloalkylene, or arylene as defined herein is optionally substituted with one or more substituents selected from the group consisting of $C_{1-6}$-alkyl, —C(O)N($C_{1-6}$-alkyl)$_2$, and —C(O)O($C_{1-6}$-alkyl).

More specific embodiments are described below.

DETAILED DESCRIPTION

Definitions

Figure 1:
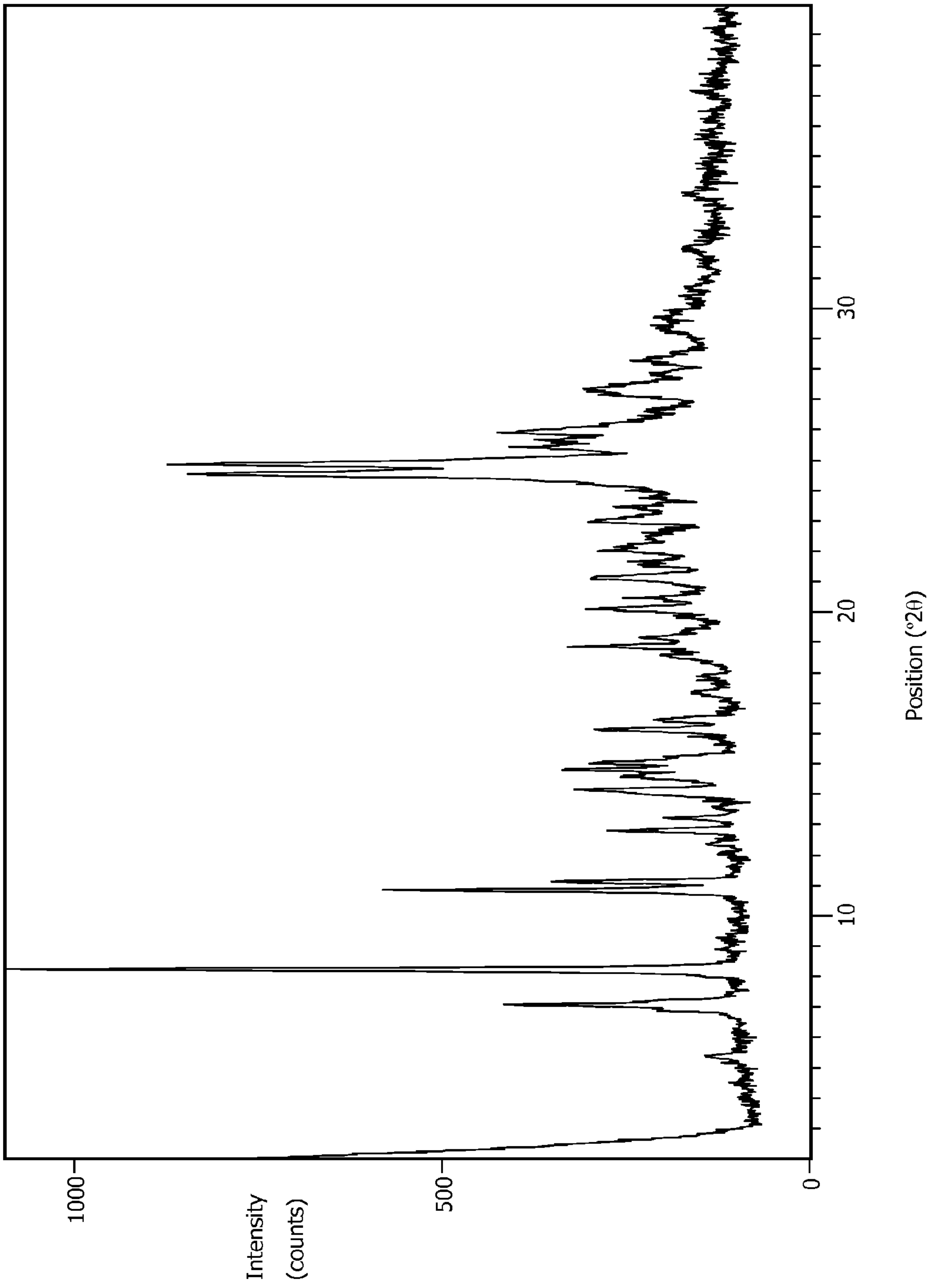
FIG. 1 is an X-ray powder diffractogram of Form I, a crystalline polymorph of compound 30 as described hereinbelow.

As used in the present specification, the following words and phrases are generally intended to have the meanings as set forth below, except to the extent that the context in which they are used indicates otherwise.

The term "alkyl" as used herein refers to a straight or branched chain, saturated hydrocarbon having the indicated number of carbon atoms. For example, ($C_1$-$C_8$)alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein throughout.

The term "substituted alkyl" refers to:

1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and $NR^a$, where $R^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2, or 3) an alkyl group as defined above that has both 1, 2, 3, 4 or 5 substituents as defined above and is also interrupted by 1-10 atoms (e.g. 1, 2, 3, 4 or 5 atoms) as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "lower alkyl" refers to a monoradical branched or unbranched saturated hydrocarbon chain having 1, 2, 3, 4, 5 or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (in some embodiments, 1, 2 or 3 substituents), as defined for substituted alkyl or a lower alkyl group as defined above that is interrupted by 1, 2, 3, 4 or 5 atoms as defined for substituted alkyl or a lower alkyl group as defined above that has both 1, 2, 3, 4 or 5 substituents as defined above and is also interrupted by 1, 2, 3, 4 or 5 atoms as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "lower alkylene" or "alkylene" refers to a diradical of a branched or unbranched saturated hydrocarbon chain, in some embodiments, having 1, 2, 3, 4, 5 or 6 carbon atoms.

The term "substituted alkylene" refers to an alkylene group as defined above having 1 to 5 substituents (in some embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —$CH{=}CH_2$), 1-propylene (or allyl, i.e. —$CH_2CH{=}CH_2$), isopropylene (—$C(CH_3){=}CH_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—$C{\equiv}CH$), propargyl (or propynyl, i.e. —$C{\equiv}CCH_3$), and the like.

The term "substituted alkynyl" refers to an alkynyl group as defined above having 1 to 5 substituents (in some embodiments, 1, 2 or 3 substituents) as defined for substituted alkyl.

The term "hydroxy" or "hydroxyl" refers to a group —OH.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is substituted alkylene and Z is substituted alkenyl or substituted alkynyl, where substituted alkyl, substituted alkenyl and substituted alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. The term "substituted cycloalkyl" also includes cycloalkyl groups wherein one or more of the annular carbon atoms of the cycloalkyl group has an oxo group bonded thereto. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "arylene" herein refers to a diradical of "aryl" as defined above that is divalent by virtue of formal removal of a hydrogen atom from the aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "amino" refers to the group —$NH_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "alkyl amine" refers to R—$NH_2$ in which R is optionally substituted alkyl.

The term "dialkyl amine" refers to R—NHR in which each R is independently an optionally substituted alkyl.

The term "trialkyl amine" refers to $NR_3$ in which each R is independently an optionally substituted alkyl.

The term "cyano" refers to the group —CN.

The term "azido" refers to a group $$—N=\overset{\oplus}{N}=\overset{\ominus}{N}.$$

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, $CF_3$, amino, substituted amino, cyano or —$S(O)_nR^a$, in which $R^a$ is alkyl, aryl or heteroaryl and n is 0, 1 or 2.

The term "acyl" denotes a group —C(O)R, in which R is hydrogen, optionally substituted alkyl, optionally substituted cycloalkyl, optionally substituted heterocyclyl, optionally substituted aryl or optionally substituted heteroaryl.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "acyloxy" refers to the groups —OC(O)-alkyl, —OC(O)-cycloalkyl, —OC(O)-aryl, —OC(O)-heteroaryl and —OC(O)-heterocyclyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. All substituents may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "alkoxycarbonylamino" refers to a group —$N(R^d)C(O)OR$ in which R is optionally substituted alkyl and $R^d$ is hydrogen or optionally substituted alkyl.

The term "aminocarbonylamino" refers to the group —$NR^cC(O)NRR$, wherein $R^c$ is hydrogen or optionally substituted alkyl and each R is independently selected from the group consisting of hydrogen, alkyl, cycloalkyl, aryl, heteroaryl and heterocyclyl. Unless otherwise constrained by the definition, all substituents may optionally be further substituted by 1, 2 or 3 substituents selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl.

The term "thiol" refers to the group —SH.

The term "thiocarbonyl" refers to a group ═S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —$S(O)_2R$, in which R is alkyl, cycloalkyl, heterocyclyl, aryl or heteroaryl. "Substituted sulfone" refers to a group —$S(O)_2R$, in which R is substituted alkyl, substituted cycloalkyl, substituted heterocyclyl, substituted aryl or substituted heteroaryl, as defined herein.

The term "aminosulfonyl" refers to the group —$S(O)_2$NRR, wherein each R is independently selected from the group consisting of hydrogen, alkyl, cycloalkyl, aryl, heteroaryl and heterocyclyl. Unless otherwise constrained by the definition, all substituents may optionally be further substituted by 1, 2 or 3 substituents selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of a given Formula (e.g. the compound of Formula I) is intended to encompass the compounds of the disclosure, and the pharmaceutically acceptable salts, pharmaceutically acceptable esters, isomers, tautomers, solvates, isotopes, hydrates, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given Formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

The term "amine protecting group" is well understood by the person skilled in synthetic organic chemistry as a moiety that can be selectively installed onto and removed from a suitable amine functional group. The field of protecting group methodology is advanced, and many amine protecting groups, and methods for using them, are well known in the art, such as those described in the authoritative treatise on the subject, P. G. M. Wuts and T. W. Greene, Greene's Protective Groups in Organic Synthesis, $4^{th}$ Edition (Wiley, 2006).

The term "borylation agent" also is well understood in the field of organic synthesis as a reagent that is useful for installing any one of a wide range of boronate moieties onto a suitable substrate. Non-limiting examples of borylation agents and related synthetic methodology are set forth in T. Ishiyama et al., *J. Org. Chem.* 1995, 60, 7508-7510.

The term "hydroxy" or "hydroxyl" refers to a group —OH.

If there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of it.

The term "solvate" refers to a complex formed by the combining of a compound of Formula I, or any other Formula as disclosed herein, and a solvent.

The term "hydrate" refers to the complex formed by the combining of a compound of Formula I, or any Formula disclosed herein, and water.

The term "prodrug" refers to compounds of Formula I, or any Formula disclosed herein, that include chemical groups which, in vivo, can be converted and/or can be split off from the remainder of the molecule to provide for the active drug, a pharmaceutically acceptable salt thereof or a biologically active metabolite thereof.

Any formula or structure given herein, including Formula I, or any Formula disclosed herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as but not limited to $^2H$ (deuterium, D), $^3H$ (tritium) $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I, or any Formula disclosed herein, in which from 1 to "n" hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula I, or any Formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. See: P. Heinrich Stahl and Camille G. Wermuth (Eds.) Pharmaceutical Salts Properties, Selection, and Use (International Union of Pure and Applied Chemistry), Wiley-VCH; 2nd Revised Edition (May 16, 2011). Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroaryl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to $NH(heteroaryl)_2$, wherein "heteroaryl" is as defined herein and so on.

Specific examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

In addition, abbreviations as used herein have respective meanings as follows:

| | |
|---|---|
| ACN | acetonitrile |
| AN | peak area normalization |
| Bn | benzyl |
| Boc | tert-butoxycarbonyl |
| Cbz | benzyloxycarbonyl |
| CDMT | 6-Chloro-2,4-dimethoxy-s-triazine |
| DCC | N,N'-Dicyclohexylcarbodiimide |
| DCE | dichloroethane |
| DCM | dichloromethane |
| dd | doublet of doublets |
| ddd | doublet of doublet of doublets |
| DIC | N,N'-Diisopropylcarbodiimide |
| DMAC | N,N-dimethylacetamide |
| DMF | dimethylformamide |

-continued

| | |
|---|---|
| DMSO | dimethylsulfoxide |
| EDC | 1-ethyl-3-(3-dimethylaminopropyl) carbodiimide |
| EtOAc | Ethyl acetate |
| HATU | 2-(7-Aza-1H-benzotriazole-1-yl)-1,1,3,3-tetramethyluronium hexafluorophosphate |
| HBTU | O-Benzotriazole-N,N,N',N'-tetramethyl-uronium-hexafluoro-phosphate |
| HOBt | hydroxybenzotriazole |
| HPLC | High pressure liquid chromatography |
| IPA | isopropyl alcohol |
| IPAc | Isopropyl acetate |
| IPE | diisopropyl ether |
| KHMDS | potassium hexamethyldisilazane |
| LDA | lithium diisopropylamide |
| LiHMDS | lithium hexamethyldisilazane |
| MeCN | acetonitrile |
| MEK | methylethyl ketone |
| MeOH | methanol |
| MePHOS | 2-Dicyclohexylphosphino-2'-methylbiphenyl |
| MIBK | methylisobutyl ketone |
| Moc | methoxycarbonyl |
| MsO or OMs | mesylate or methansulfonate |
| MTBE | methyl-tert-butyl ether |
| NaHMDS | sodium hexamethyldisilazane |
| NFSI | N-fluorobenzenesulfonimide |
| NMM | N-methylmorpholine |
| NMP | N-methylpyrrolidine |
| OAc | acetate |
| PG | Protecting group |
| $PPh_3$ | triphenylphosphine |
| SMB | Simulated moving bed |
| TFA | trifluoroacetic acid |
| THF | tetrahydrofuran |

Processes

As described generally above, the disclosure provides in some embodiments processes for making a compound of formula I. Step A, concerning the coupling of compounds according to formulae (i) and (ii), respectively, provides yet additional embodiments. For instance, in one embodiment, a compound of formula (i) is the boronate coupling partner, wherein Y is —B(OR)(OR') and, therefore, in formula (ii) substituent Z is Br.

One advantage of the disclosure is provided in another embodiment, whereby the compound of formula (i) is generated in situ, thereby allowing subsequent coupling step A to proceed in one pot. In this embodiment, the process comprises sequentially contacting a compound of formula (a)

(a)

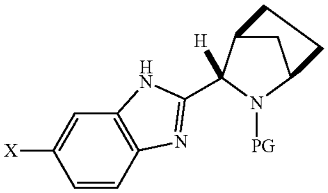

with a source of palladium and then a borylation agent comprising the moiety

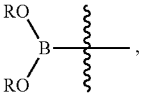

in the presence of a second base, whereby the compound of formula (i) is formed in situ, and wherein PG is as defined above and X is a halide selected from Cl, Br, and I. In some embodiments, the borylation reagent is selected from bis (pinacolato)diboron and bis(neopentylglycolato)diboron. Thus, in one embodiment, the borylation reagent is bis(neopentylglycolato)diboron. In another embodiment, the borylation reagent is bis(pinacolato)diboron.

In another embodiment of the process for making a compound of formula (i), the halide X is Br and the protecting group PG is tert-butoxycarbonyl.

In some embodiments of the processes described above, the metal catalyst is chosen from Pd(0) and Pd(II) compounds. The exact oxidation state of Pd is not critical so long as a catalytically active Pd(0) species is produced in accordance with well-established conditions for Suzuki couplings. Thus, for instance, in some embodiments, the metal catalyst is $PdCl_2[P(t\text{-}Bu)_2Ph]_2$. In other embodiments, the catalyst is $Pd(OAc)_2$/2-dicyclohexylphosphino-2'-methylbiphenyl. In still another embodiment, the catalyst is dichloro[1,1'-bis (diphenylphosphino)ferrocene]palladium(II)dichloromethane adduct.

Other metal catalysts are acceptable, such as those formed from Pd or Ni in combination with ligands that are added to a reaction mixture. Typical ligands include 1,1'-bis(diphenylphosphino)ferrocene, triphenylphosphine, tri(2-methoxyphenyl)phosphine, tricyclohexylphosphine, 2-(dicyclohexylphosphino)biphenyl, 2-dicyclohexylphosphino-2'-methylbiphenyl, 2-(dicyclohexylphosphino)-2'-(N,N-dimethylamino)biphenyl, 2-(di-tert-butylphosphino)-2'-(N,N-dimethylamino)biphenyl, dicyclohexyl(2,2-diphenyl-1-methylvinyl)phosphine, bis(2-dicyclohexylphosphinophenyl)ether, dicyclohexyl(4-(N,N-dimethylamino)phenyl)phosphine, 2-dicyclohexylphosphino-2'-fluorobiphenyl, 2-dicyclohexylphosphino-2',6'-difluorobiphenyl.

Alternatively, it is possible to employ preformed metal/ligand systems such as dichloro[1,1'-bis(diphenylphosphino) ferrocene]palladium(II), bis[di-tert-butyl(4-dimethylaminophenyl)phosphino]palladium(II)chloride, and bis[di-(tert-butyl)(4-trifluoromethylphenyl)phosphine]palladium(II) chloride. All of these possibilities are contemplated in this disclosure.

The borylation process of making a compound of formula (i) as described above is performed in the presence of a second base, which is not necessarily the same as the base employed for Step A. Thus, in one embodiment, the second base is a propionate salt, such as potassium propionate. Other bases also are suitable for this purpose, and they include acetates such as sodium, potassium or cesium acetate; and phosphates such as sodium or potassium phosphate.

Another embodiment provides a further process for making a compound of formula I:

(I)

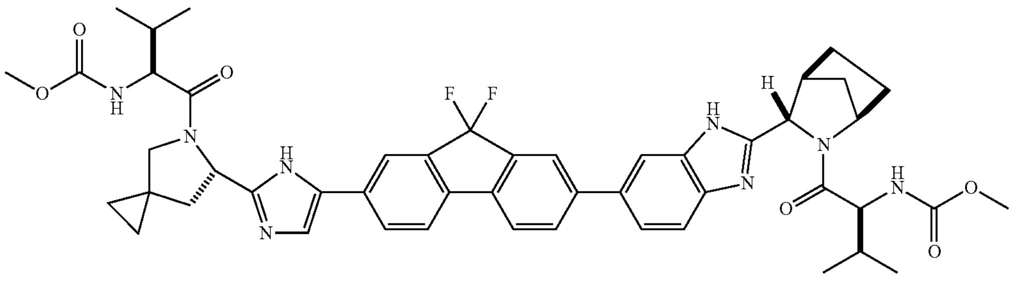

or a pharmaceutically acceptable salt thereof. In this embodiment, the process comprises the steps of (1) sequentially contacting a compound of formula (a')

(a')

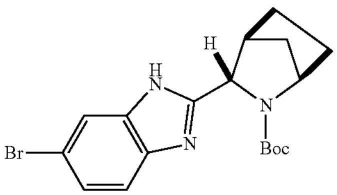

with a catalytically effective amount of $PdCl_2[P(t\text{-}Bu)_2Ph]_2$ and bis(neopentylglycolato)diboron in the presence of potassium propionate to yield a reaction mixture comprising a compound of formula (ia):

(ia)

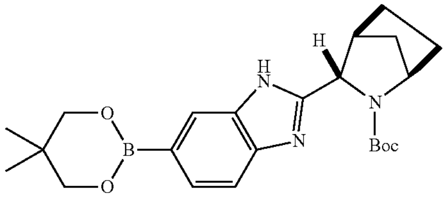

;

Step (2) of the process is contacting the reaction mixture from step (1) with a compound of formula (ii'):

(ii')

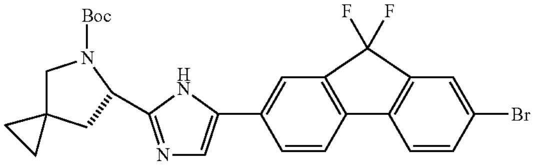

and potassium phosphate to yield a compound of formula (iii'):

(iii')

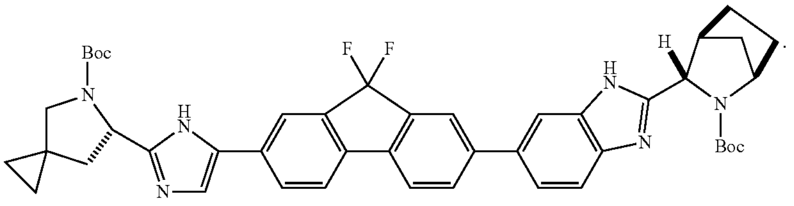

In some embodiments, the compound of formula (iii') optionally is contacted with oxalic acid to yield an oxalate salt according to formula (iii"):

(iii")

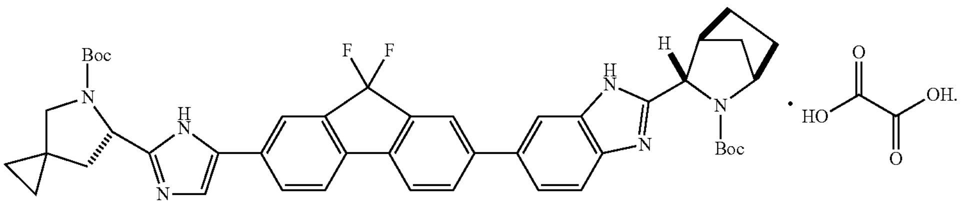

Step (3) of the process is contacting the compound of formula (iii') or formula (iii") with HCl to yield a compound of formula (iv'):

(iv')

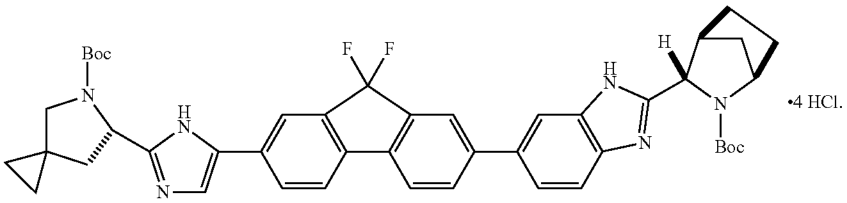

Finally, step (4) is contacting the compound of formula (iv') with (S)-2-(methoxycarbonylamino)-3-methylbutanoic acid:

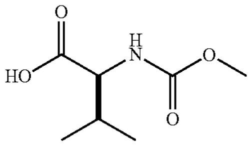

to yield a compound of formula I. In the structures depicted above, "Boc" in each instance represents tert-butoxycarbonyl. Other salts corresponding to compound iv' can be used in variations of this reaction, proceeding from the generation of salts as defined herein. In some embodiments, step (4) is performed with the free base of compound iv'.

In an alternative embodiment, the process as described immediately above can be carried out by employing in step (1) a boronated intermediate compound of formula (ib) instead of (ia):

(ib)

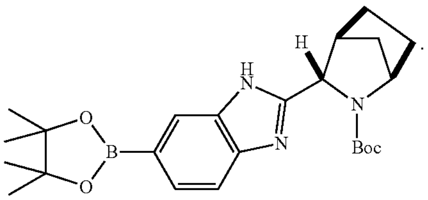

Compound (ib) is prepared in a reaction between compound (a') as defined above and bis(pinacolato)diboron in the presence of a catalytically effective amount of $PdCl_2[P(t-Bu)_2h]_2$ and potassium propionate.

Compounds

In other embodiments, the disclosure provides for intermediate compounds that are useful in the processes described herein. Thus, for instance, one embodiment is a compound of formula (ii):

(ii)

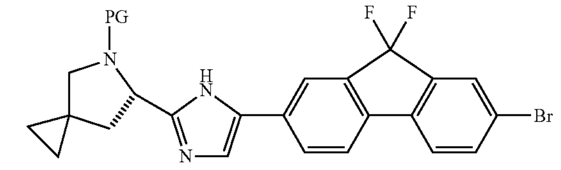

wherein PG is an amine protecting group as defined hereinabove. An exemplary compound of formula (ii) is defined where PG represents tert-butoxycarbonyl.

In another embodiment, the disclosure provides a compound of formula (iii'):

(iii')

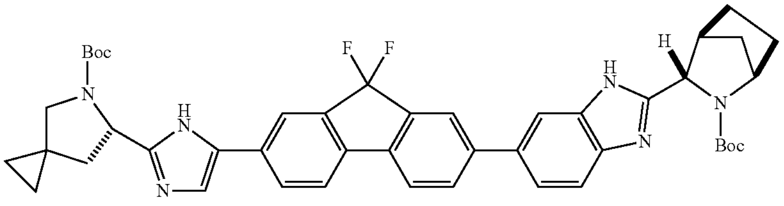

or an oxalate salt thereof according to formula (iii"):

(iii")

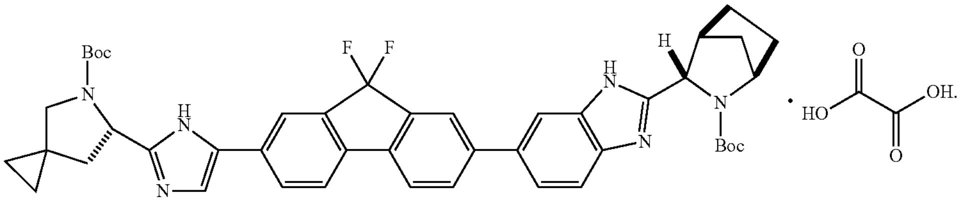

In yet another embodiment, the disclosure provides a compound of formula (iv):

(iv)

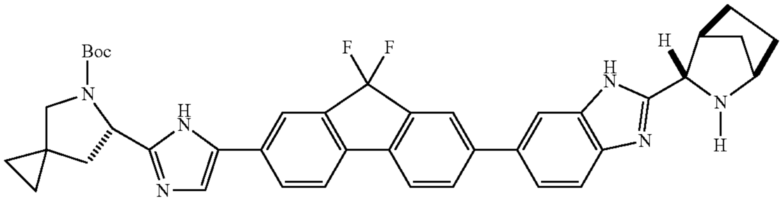

or a salt, hydrate, and/or solvate thereof. For example, a specific embodiment is the compound of formula (iv'), a tetrahydrochloride salt:

(iv')

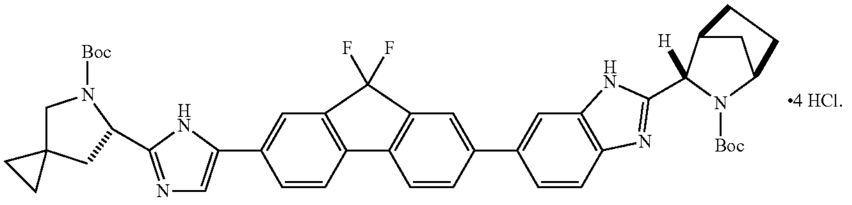

Another embodiment is a hydrate of a compound of formula (iv') according to the following formula:

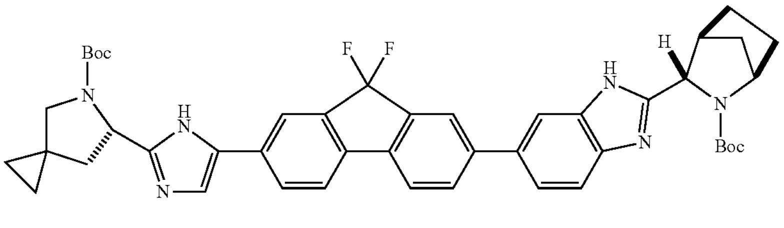

•4 HCl•$(H_2O)_q$, wherein q is a number, fractional or otherwise, between 0 and 7. In other words, the hydrate is a compound that can have integer or fractional equivalents of waters present. For example, a typical hydrate is wherein q is a number between 0 and 6, such as between 2 and 6 or between 5 and 6.

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms or methyl groups can be omitted from the drawn structures consistent with accepted shorthand notation of such organic compounds, and that one skilled in the art of organic chemistry would readily appreciate their presence

EXAMPLES

I. Synthesis of Starting Materials

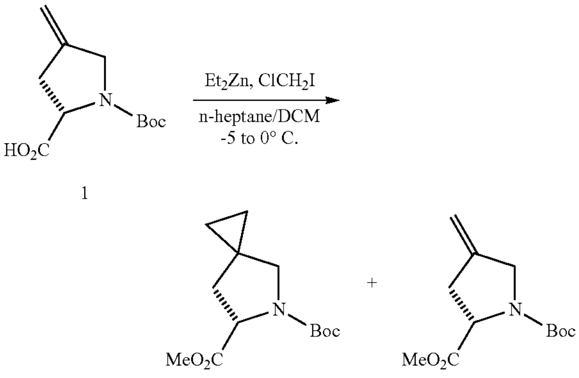

1

2 3

A. Cyclopropanation to Prepare 2

To a solution of DCM (1.5 L) and n-heptane (0.32 L) at ambient temperature was added diethyl zinc (800 mL, 1.0 M in n-heptane). The reaction mixture was cooled to 0° C., and a solution of compound 1 (45.0 g) in DCM (250 mL) was added over 10 min. Upon completion of the addition, the reaction mixture was cooled to −5° C. and chloroiodomethane (176 g) was charged via syringe pump over 3.5 h. The reaction mixture was stirred at −5° C. for an additional 16 h and was quenched by the slow addition (1 h) of 1N aqueous HCl (1.4 L). After warming to 20° C., the phases were separated, and the aqueous layer was back extracted with DCM (0.5 L). The combined organic layers were washed with 10% aqueous NaCl (1.2 L), the phases were separated, and the organic layer was concentrated in vacuo to provide a crude oil that was purified by flash chromatography on silica gel (50 ethyl acetate/n-heptane). The desired product was isolated as a mixture of compounds 2 and 3 (46.6 g, 67.5 wt % compound 2, 62% corrected yield.)

In alternative embodiments, the cyclopropanation also can be achieved with diethyl zinc and diiodomethane in a variety of solvents. For instance, dichloromethane, dichloroethane, toluene, hexanes, and combinations thereof are suitable for this purpose. In addition, the cyclopropanation can be performed at a temperature of about −20° C. to about 20° C., though typical temperatures are between −5° C. and 0° C.

B. Hydrolysis/Iodolactonization

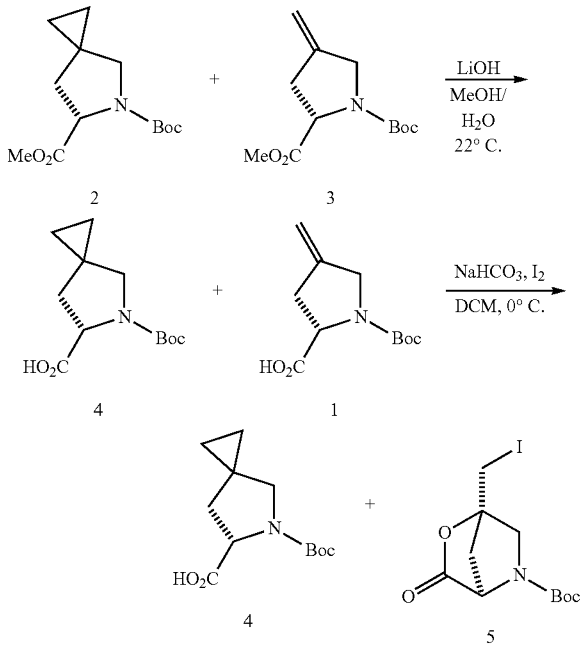

2 3

4 1

4 5

Hydrolysis/Iodolactonization to Prepare 4:

A mixture of compounds 2 and 3 (161.80 g, 59 wt % compound 2) was dissolved in MeOH (1.2 L). Water was added, the mixture was cooled to 15° C. and solid LiOH.$H_2O$ (32.8 g) was charged. The reaction mixture was warmed to 25° C. and stirred for 13.5 h. The reaction mixture was then concentrated in vacuo to remove the MeOH, and DCM (1 L) and water (200 mL) were added. The resulting mixture was cooled to 10° C., and 2 N aqueous HCl (375 mL) was added. Following separation of the phases, the aqueous layer was extracted with DCM (2×500 mL, then 250 mL). The combined organic layers were dried over $Na_2SO_4$, filtered and concentrated in vacuo to 1.2 L. To this solution was added water (305 mL), $NaHCO_3$ (136 g) and $I_2$ (90.7 g). The reaction mixture was stirred at 25° C. for 40 h and diluted with 8% aqueous $NaHCO_3$ (750 mL), water (750 mL) and DCM (300 mL). Following phase separation, the combined organic layer was extracted water (1 L). The combined aqueous layers were then washed with isopropyl acetate (300 mL), cooled to 0° C. and acidified by the addition of 2 N aqueous HCl (1.1 L). The aqueous phase was extracted with DCM (3×1 L), and the combined organic layer was washed with 10% aqueous $NaHSO_3$ (2 L) and 10% aqueous NaCl (1.5 L). The organic layer was dried over $Na_2SO_4$, filtered and concentrated in vacuo. The resulting solid was twice dissolved and re-concentrated from isopropyl acetate (1 L). Additional isopropyl acetate (100 mL) was charged to the solid, the solution was heated to 50° C. and n-heptane (800 mL) was added. After cooling to 20° C. over 4 h, the slurry was cooled to 5° C. aged for 2 h. The product was collected by filtration, washed with n-heptane (2×150 mL) and dried to afford compound 4 as a light yellow solid (66.5 g, 74% yield from compound 2). $^1H$ NMR (400 MHz, $d_6$-DMSO, δ): 12.5 (s, 1H) 4.23-4.17 (m, 1H), 3.32-3.16 (m, 2H), 2.28-2.22 (m, 1H), 1.74 (dd, J=12.7, 4.3 Hz, 0.6H rotamer 1), 1.67 (dd, J=12.7, 3.7 Hz, 0.4H rotamer 2), 1.39 (s, 4H rotamer 1), 1.35 (s, 5H rotamer 2), 0.59-0.45 (m, 4H). $^{13}C$ NMR (100 MHz, $d_6$-DMSO, δ): 173.9, 173.5, 153.4, 153.0, 78.7, 78.6, 59.1, 58.8, 53.7, 53.4, 38.2, 37.5, 28.1, 27.9, 20.5, 19.9, 12.2, 11.5, 8.8, 8.3.

In some embodiments, the hydrolysis is achieved by use of other bases, such as potassium or sodium hydroxide. In yet other embodiments, alternative solvent combinations are suitable for this purpose, such as ethanol/water, isopropyl alcohol/water, and THF/water.

The hydrolysis can be performed at a temperature of about 0 to about 80° C. A typical temperature is ambient, such as 22° C.

Other solvents and solvent combinations are suitable for the iodolactonization. For instance, these include dichloroethane, toluene, ethers, THF or 2-methyl THF, ethyl acetate, and isopropyl acetate.

Acceptable iodolactonization temperatures range from about 0 to about 50° C. A typical and convenient temperature is about 22° C.

Some embodiments of the iodolactonization reaction provide for other bases, such as potassium bicarbonate ($KHCO_3$), dipotassium carbonate ($K_2CO_3$), and disodium carbonate ($Na_2CO_3$).

C. Iodination of Diol 6

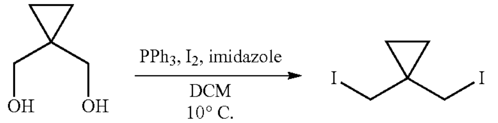

6

7a

1. Iodination of 6 to Prepare 7a:

Triphenylphospine (257.2 g) and imidazole (66.7 g) were charged to a reactor. DCM (490 mL) was charged, agitation was initiated and the solution was cooled to 0° C. Iodine (249.2 g) was added as a solid portion-wise over 1 h while maintaining the internal temperature below 10° C. Upon completion of the addition, a solution of 6 (50 g) in DCM (113 mL) was slowly charged to the reactor over 0.5 h while maintaining the internal temperature below 10° C. After stirring for 2.5 h, an aqueous solution of NaCl (25 g) in water (225 mL) was charged to the reactor. Following phase separation, the bottom organic layer was diluted with n-heptane (550 mL). The organic phase was washed with an aqueous solution of sodium sulfite (21 g) in water (190 mL). Following layer separation, the organic phase was concentrated to 600 mL via vacuum distillation. Additional n-heptane (550 mL) was charged, and the mixture was again concentrated to 600 mL via vacuum distillation. The resulting slurry was filtered over a silica gel plug (85 g) that had been slurry packed with n-heptane. The silica gel plug was rinsed with additional n-heptane (1 L), and the filtrate was then concentrated via vacuum distillation to provide the desired product 7a as a colorless liquid (114 g, 70%). $^1H$ NMR (400 MHz, $CDCl_3$) δ 3.33 (s, 2H), 0.95 (s, 2H). $^{13}C$ NMR (75 MHz, $CDCl_3$): 19.1, 22.7, 26.0.

It is also possible, in accordance with other embodiments, to effect the iodination with trimethylsilyl chloride and sodium iodide in acetonitrile. Suitable temperatures for this reaction range from about −10 to about 30° C.

2. Alternative Procedure

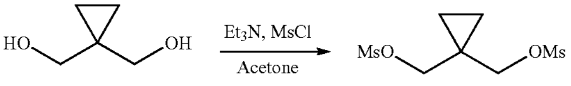

6

1,1-Bis(hydroxymethyl)cyclopropane (40.00 g, 388 mmol) was added to a flask followed by acetone (400 mL, 15 vol) and the reaction was cooled to 0° C. Triethylamine (87.16 g, 861 mmol, 2.2 eq.) was added to the reaction and then methanesulfonyl chloride (98.68 g, 861 mmol, 2.2 eq) was added slowly such that the internal temperature does not rise above 10° C. A white precipitate forms during the addition of methanesulfonyl chloride. After the addition is complete, the reaction was allowed to stir at 0° C. for 1 h and then warmed to 20° C. and allowed to stir for 2 hours.

Once the reaction was judged complete, 800 mL (30 volumes) water were added and the reaction was stirred for 15 minutes. The reaction was then filtered and washed with 100 mL water. The product was isolated on the filter as a white solid. Upon drying under vacuum at 20° C., yield 85.5 g, 86%. $^1H$ NMR (400 MHz, $CDCl_3$) δ 4.16 (s, 2H), 3.06 (s, 3H), 0.83 (s, 2H).

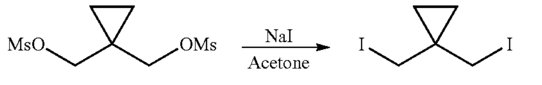

7a

The bis-mesylate compound (26.5 g, 102.5 mmol) and sodium iodide (46.1 g, 307.5 mmol, 3 equiv) were added to a round bottom flask with overhead stirring and temperature probe followed by acetone (400 mL). The flask was heated to 35° C. internal. The reaction turned yellow/orange and precipitate formed over time. Typical reaction time was 6-7 h. Once the reaction was judged complete, the reaction was filtered and washed forward with 100 mL acetone. The liquors were then concentrated to a ~150 mL and 300 mL of aqueous 5% sodium sulfite solution was added. Hexanes (200 mL) were added and the mixture was agitated for a minimum of 15 minutes. The layers were allowed to separate and the top organic layer was dried over sodium sulfate (20 g). The organic layer was then filtered to remove the sodium sulfate and concentrated to an oil. Yield 31.0 g, 94%.

D. Alkylation of 8 to Prepare 9

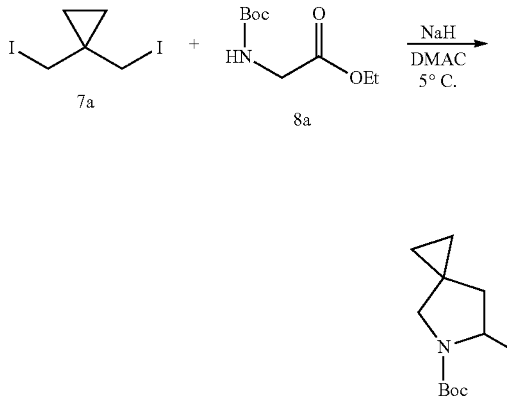

7a 8a 9a

Sodium hydride (60.0 g, 3 equivalents, 60% dispersion in mineral oil) and dimethylacetamide (600 mL) were charged to a flask and the reaction temperature was lowered to 0-10° C. Compound 7a (191.6 g, 1 equivalent) was charged to the NaH solution once the internal temperature was approximately 5° C. A solution of compound 8a (121.0 g, 1 equivalent) in DMAC (600 mL) was added over 3.5 h, keeping the internal temperature between 0-11° C. The solution was stirred at 0-10° C. and sampled for reaction completion after 1 h. The reaction was considered complete when the remaining amount of 8a was less than 3%. Upon completion, AcOH (50 mL, 1.5 equivalents) was slowly added over 2-3 h while keeping the temperature between 4-9° C. The solution was stirred for 12 h at 0-10° C. MTBE (1000 mL) and water (700 mL) were added to the quenched solution. The layers were separated and the aqueous layer was extracted with MTBE (400 mL). The organic layers were combined and washed once with a 15% NaCl solution (1000 mL), once with a 5% sodium bicarbonate solution (900 mL) and once with a brine solution (600 mL). The MTBE solution was concentrated to a minimum volume. The oil was re-dissolved in ACN (400 mL) and washed with hexanes (200 mL). The phases were separated, the ACN layer was concentrated to a minimum volume and the hexanes layer was discarded. The product 9a was isolated as a yellow oil (98 g, 61%). $^1$H NMR (400 MHz, $CDCl_3$) δ 4.45 (dd, J=8.5, 3.7 Hz, 0.5H rotamer 1), 4.35 (dd, J=8.4, 4.4 Hz, 0.5H rotamer 2), 4.27-4.11 (m, 2H), 3.44-3.29 (m, 2H), 2.26 (ddd, J=12.7, 8.4, 4.1 Hz, 1H), 1.80 (ddd, J=23.5, 12.6, 4.0 Hz, 1H), 1.58, 1.48-1.40 (m, 9H), 1.32-1.21 (m, 3H), 0.68-0.44 (m, 4H).

In some embodiments, other suitable non-nucleophilic bases are used. These include alkoxides such as tert-butoxides of lithium, sodium, and potassium.

Solvents other than DMAC also are acceptable. For instance, these include N-methylpyrrolidine, dimethylformamide, and 1,3-dimethyl-3,4,5,6,-tetrahydro-2-pyrimidinone.

In the example above, Boc is the amine protecting group. In some embodiments, however, protecting groups other than Boc are used, such as methyloxy and isopropyloxy carbonyls. The protecting group also can be Cbz.

Suitable temperatures for carrying out the reaction range from about −10 to about 40° C.

Alternate Alkylation Sequence

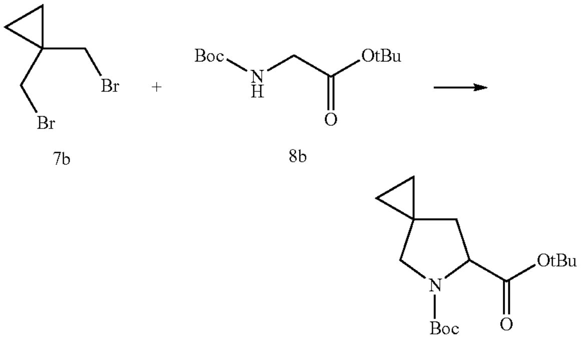

7b 8b 9b

To a cooled (0° C.) solution of the N-Boc-glycine t-butyl ester 8b (10.66 g; 46 mmol) and the dibromide 7b (10.1 g; 44.3 mmol) in N,N-dimethylformamide (50 mL) was added potassium t-butoxide (13.79 g; 122.8 mmol). The resulting slurry was then warmed to 20° C. and agitated at that temperature for 4 hours. The reaction contents were then poured in to a stirring solution of Me-THF (100 mL) and water (100 mL). The resulting organic solution was subsequently dried and concentrated under vacuum to give an amber oil. The crude material was then purified by silica gel chromatography (90:10 hexanes:ethyl acetate) to afford the product t-butyl ester 9b as a colorless oil (5.5 g, 42% yield). $R_f$: 0.18 ($SiO_2$, 9:1 hexanes:ethyl acetate). $^1$H NMR (400 MHz, $CDCl_3$): δ 4.33 (rotamer #1: dd, J=8.4, 2.9 Hz, 0.35H); 4.24 (rotamer #2: dd, J=8.6, 3.3 Hz, 0.65H); 3.42 (rotamer #2: d, J=10.2 Hz, 0.65H); 3.36 (rotamer #1: d, J=10.2 Hz, 0.35H); 3.28 (rotamer #2: d, J=10.2 Hz, 0.65H); 3.22 (rotamer #1: d, J=10.2 Hz, 0.35H); 2.31 (rotamer #2: dd, J=12.7, 8.6 Hz, 0.65H); 2.26 (rotamer #1: dd, J=12.7, 8.6 Hz, 0.35H); 1.70 (m, 1H); 1.46 (m, 18H); 0.54 (m, 4H). $^{13}$C NMR (100 MHz, $CDCl_3$, δ): 172.0, 153.9, 80.8, 79.6, 79.4, 60.3, 60.1, 54.1, 53.7, 39.2, 38.3, 28.4, 28.3, 27.9, 20.5, 19.8, 13.4, 13.3, 8.3.

In some embodiments, other reaction temperatures are used. The reaction temperature can be between −50° C. and 50° C.

E. Hydrolysis of Ethyl Ester 9.

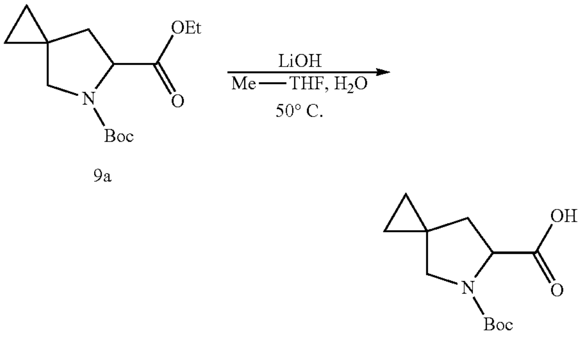

9a 17

Hydrolysis to 17

Water (910 mL), lithium hydroxide (284 g, 2.0 eq) and 2-MeTHF (2.0 L) were added to a flask equipped with overhead stirring, an internal thermometer and a nitrogen line. A solution of compound 9a (911 g) in 2-MeTHF (1.0 L) was transferred into the flask containing the lithium hydroxide.

The reaction was heated to 50° C. until the reaction was deemed complete as determined by HPLC analysis. The reaction was cooled to 22° C. and water (3.6 L) was added to the reaction. The layers were split and the bottom aqueous layer was retained while the upper organic layer was eliminated. 2-MeTHF (4 L) and concentrated HCl (420 mL) were added to the aqueous layer. The layers were separated and the bottom aqueous layer removed. The upper organic layer was concentrated and the product 17 isolated as a white solid (596 g, 71%). Characterization data for 17 is the same as for compound 4 described above.

Alternatively, bases other than LiOH can be used. Thus, in some embodiments, the base is potassium hydroxide, sodium hydroxide, or potassium silanolate.

In other embodiments, the solvent can vary. Suitable solvents include, for example, dialkyl and cyclic ethers, toluene, and dichloromethane.

Typical reaction temperatures range from about 0 to about 80° C. In the example above, the temperature is 50° C.

F. Classical Resolution

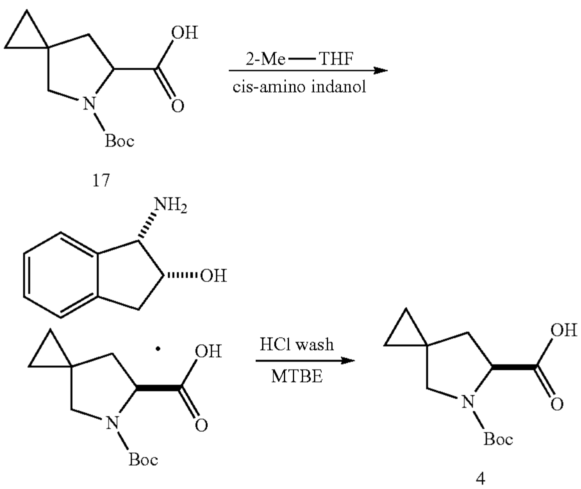

17

18a

4

Classical Resolution to 4:

Racemic carboxylic acid 17 (596 g) was dissolved in 2-Me-THF (6 L) and then the homogenous solution was heated to 55° C. (1S,2R)-amino-indanol (221 g, 0.6 eq) was added to the reaction in 3 equal portions 10 minutes apart. The solution was seeded with salt 18a (0.6 g) after the first portion had been added. After the last portion of amine was added the solution was aged at 55° C. for 1 h. The slurry was then cooled to 22° C. at a rate of ~15 degrees per hour. Once the slurry had reached room temperature it was filtered and the cake was washed once with 2-Me-THF (1.2 L). The solids were dried at 45° C. in a vacuum oven for 24 h. Compound 18a was isolated as a white solid (320 g, 33%).

The solids 18a were dissolved in MeTHF (1.5 L), 1M HCl (1.0 L) was added and the biphasic mixture stirred 30 min until the solids were dissolved. The lower aqueous layer was removed and the organic layer was washed with 1M HCl (1 L) and then $H_2O$ (500 mL). The organic layer was dried over $MgSO_4$ (250 g each) for 20 min, filtered and the cake was washed with MeTHF. This same drying procedure was repeated a second time and then the solution was concentrated to an oil to yield 4 (197 g, 100%).

In other embodiments of the classical resolution route, resolving agents are chosen from (S)-(−)-1-methylbenzylamine and (1S,2R)-(+)-norephedrine as two examples. Alternative solvents include dialkyl ethers and cyclic ethers, dichloromethane, and alkyl acetates, such as ethyl acetate. Suitable anti-solvents include, for example, hexanes and heptanes. In some embodiments, reaction temperatures range from about 0 to about 75° C.

Alternate Example of Classical Resolution:

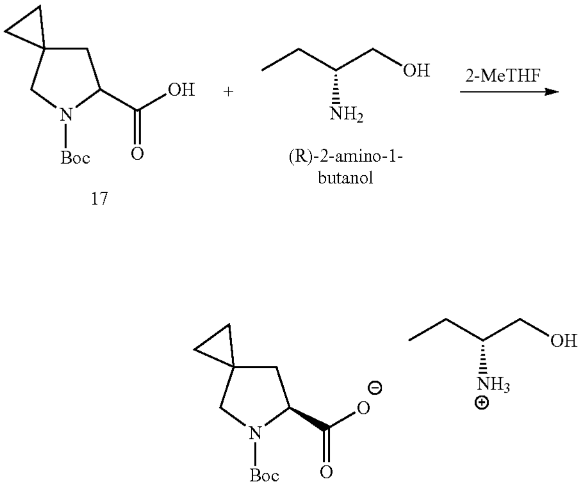

17 (R)-2-amino-1-butanol

18b

To a solution of racemic carboxylic acid 17 in 2-methyltetrahydrofuran (47 wt % 17; 52.3 g, 217 mmol) was added 2-methyltetrahydrofuran (520 mL). To this diluted solution was then added (R)-2-amino-1-butanol (13.5 g, 152 mmol) and the resulting slurry was agitated at 20° C. for a minimum of 20 hours. The reaction contents were then filtered and the solids were washed with heptane (100 mL) and dried under vacuum at 40° C. to afford the product ammonium carboxylate 18b as a white crystalline solid (22.6 g, 32% yield). $^{1}H$ NMR (400 MHz, $CDCl_3$, δ): 4.90 (s, broad, 4H); 4.25 (rotamer #1: dd, J=8.4, 4.5 Hz, 0.5H); 4.21 (rotamer #2: dd, J=8.2, 5.7 Hz, 1H); 3.76 (dd, J=11.7, 3.7 Hz, 1.5H); 3.55 (dd, J=11.7, 6.6 Hz, 1.5H); 3.43 (rotamer #2: d, J=10.3 Hz, 1H); 3.34 (rotamer #1: m, 1H); 3.26 (rotamer #2: d, J=10.2 Hz, 1H); 3.10 (dddd, J=6.8, 6.8, 6.8, 3.7 Hz, 1.5H); 2.19 (rotamer #1: dd, J=12.5, 8.6 Hz, 0.5H); 2.14 (rotamer #2: dd, J=12.3, 8.2 Hz, 1H); 1.91 (rotamer #2: dd, J=12.5, 5.7 Hz, 1H); 1.84 (rotamer #1: dd, J=12.5, 4.7 Hz, 0.5H); 1.67 (m, 3H); 1.46 (m, 12H); 1.04 (t, J=7.4 Hz, 4.5H); 0.58 (m, 6H). $^{13}C$ NMR (100 MHz, $CDCl_3$, δ): 180.4, 156.5, 80.8, 80.5, 63.5, 63.0, 62.0, 55.9, 55.6, 55.0, 40.8, 40.2, 28.9, 28.8, 23.7, 21.8, 21.4, 12.5, 11.5, 10.9, 10.2, 9.9.

G. Simulated Moving Bed (SMB) Chromatography and Hydrolyis of Ethyl Ester 19.

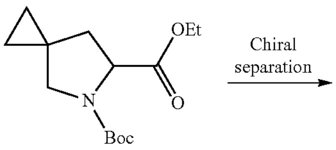

9a

-continued

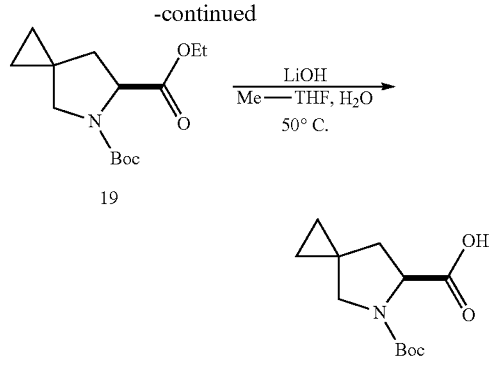

19

4

SMB and Hydrolysis to 4

Compound 9a was separated by chiral chromatography using either Chiralpak® IC or Chiralpak® IA with an appropriate mobile phase, such as a mixture of MTBE and heptane. The output of the SMB separation is concentrated to deliver compound 19 as a solution that is used directly in the next step. An assay yield of the solution is used to determine the product quantity present. Other chromatographic techniques known in the art also are useful for separation of compound 9a. These include various implementations of high performance liquid chromatography (HPLC), such as normal and reversed phase chiral HPLC; and normal chiral column chromatography, and supercritical fluid chromatography (SFC).

Water (910 mL), lithium hydroxide (284 g, 2.0 eq) and 2-MeTHF (2.0 L) were added to a flask equipped with overhead stirring, an internal thermometer and a nitrogen line. A solution of 19 (911 g) in 2-MeTHF (1.0 L) was transferred into the flask containing the lithium hydroxide. The reaction was heated to 50° C. until the reaction was deemed complete as determined by HPLC analysis. The reaction was cooled to 22° C. and water (3.6 L) was added to the reaction. The layers were split and the bottom aqueous layer was retained while the upper organic layer was removed. 2-MeTHF (4 L) and concentrated HCl (420 mL) were added to the aqueous layer. The layers were split and the bottom aqueous layer removed. The upper organic layer was concentrated and isolated the product as a white solid (596 g, 71%).

Suitable chiral phases for the SMB step above are well known in the art. Two examples are Chiralpak® IC and Chiralpak® IA.

In some embodiments, the hydrolysis reagent is chosen from alternatives such as potassium hydroxide, sodium hydroxide, and potassium silanolate. Solvent systems also can be varied and selected from dialkyl ethers and cyclic ethers, toluene, and dichloromethane, as some examples. Suitable reaction temperatures range from about 0 to about 80° C.

H. Enzymatic Resolution

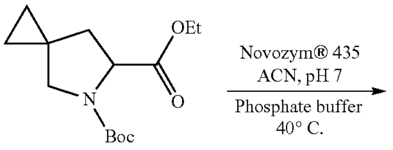

9a

-continued

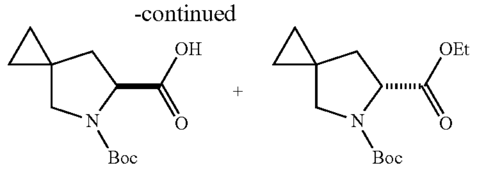

4 16

Enzymatic Resolution to 4

To a solution of 0.2 M pH 7 phosphate buffer (104 g) was charged Novozym® 435 (4 g), followed by a solution of 9a (10 g, 37.2 mmol) in MeCN (10 mL). The mixture was heated to 40° C., and the pH was adjusted as necessary using 1.0 M aqueous NaOH to maintain the pH within a range of 6.9-7.1. Upon reaction completion, the mixture was passed through a filter and the filter cake rinsed with 5% $NaHCO_3$ solution (50 g). The collective filtrate was washed with MTBE (18.4 mL). The MTBE layer was then back-extracted with 5% $NaHCO_3$ solution (8.8 g). The organic was discarded. To the combined aqueous layers was charged MTBE (8.4 mL) and enough concentrated HCl to achieve a pH of ≤2 in the aqueous phase. Following a second MTBE (5.1 mL) extraction of the acidic aqueous, the organics were combined and slurried with $MgSO_4$. The slurry was filtered, rinsing forward with MTBE. The filtrate was then concentrated via distillation. The amount of crude oil isolated was 3.40 g (75.9% yield; >99% ee).

Other enzyme reagents are acceptable for carrying out the resolution. For instance, any alternate lipase forms of *Candida Antarctica* Lipase B are effective for this transformation. Some embodiments provide for variations in solvent, which include dialkyl ethers, cyclic ethers, acetone, and dimethylsulfoxide (DMSO). Reaction temperatures vary from about 22 to about 50° C.

The disclosure provides, in another embodiment, an alternative to the foregoing procedures to make compound 4. The synthesis scheme below illustrates this embodiment:

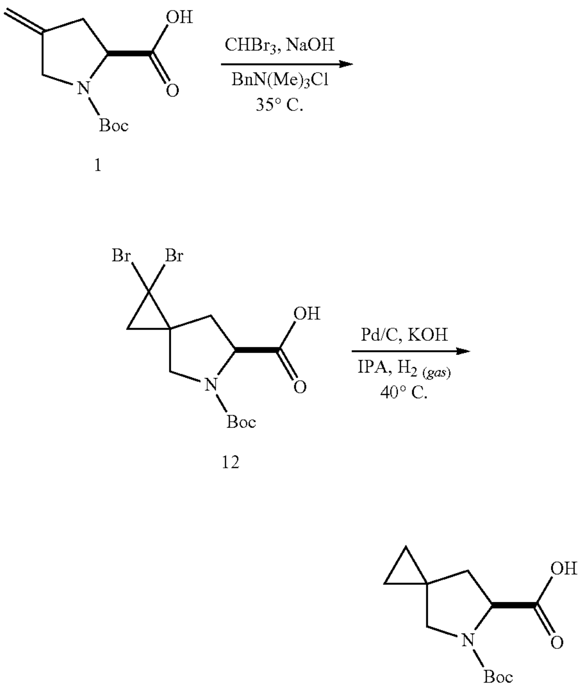

1

12

4

I. Cyclopropanation

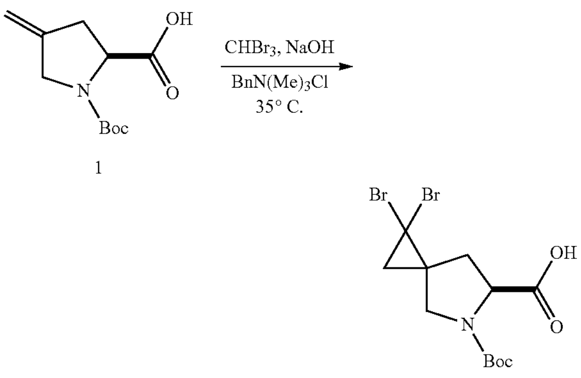

1

12

Cyclopropanation to 12

Thus, compound 1 (40.0 g, 1.0 eq), $BnN(Me)_3Cl$ (2.3 g, 0.07 eq), bromoform (45 mL, 3.0 eq) and DCM (280 mL) were added to a flask. The resultant solution was agitated at 33° C. and 50% sodium hydroxide solution (120 mL) was added over 1.5-2 hours (internal temperature did not exceed 38° C.). The solution was aged at 33° C. until the reaction was deemed complete as determined by HPLC analysis. The contents of the flask were cooled to 22° C., water (100 mL) was charged and the layers were allowed to settle for 2 hours. The bottom, aqueous layer was removed and the upper organic layer was washed with 4 M HCl (120 mL). The bottom organic layer was held and the upper aqueous layer was removed. The organic layer was then washed with water (80 mL). The lower organic layer was slurried with silica gel (12 g) for 1 hour. The silica gel was filtered off and the waste cake was washed once with DCM (80 mL). The volume of the DCM solution was reduced and the temperature of the solution was adjusted to 35° C. Heptane was charged to the reactor via a metering pump over a period of 1.5 hours. Seed crystals of compound 12 were charged to the reactor and the slurry was agitated at moderate speed for at least 60 minutes. The slurry was cooled to 20° C. (15-25° C.) over a period of 1 hour and aged at this temperature for 12 hours. The slurry was filtered at 20° C. in an appropriate filter. The filter cake was washed with a heptane (64 mL) and DCM (16 mL) solution. The product was dried at 40° C. to afford 12 as a light brown solid (47 g, 68% as a 85:15 mixture of diastereomers).

$^1$H NMR (400 MHz, $CDCl_3$, δ): 4.64-4.53 (m, 1H), 3.93-3.87 (m, 1H), 3.50 (d, J=11.1 Hz, 0.4H), 3.29 (d, J=11.1 Hz, 0.6H), 2.84 (d, J=9.6 Hz, 0.25H), 2.66 (dd, J=13.2, 8.8 Hz, 0.75H), 2.24 (d, J=13.4 Hz, 1H), 2.07-1.69 (m, 2H), 1.47 (m, 9H).

An alternative embodiment provides for the use of chloroform, which will produce the dichloro analog of compound 12, which can then be carried through subsequent steps as described below.

Bases other than NaOH also are suitable. These include potassium hydroxide and potassium tert-butoxide as two examples.

Solvents also can be varied. For instance, suitable solvents include toluene, benzene, dialkyl ethers and cyclic ethers.

Typical reactions temperatures range from about 0 to about 60° C.

J. Hydrogenation

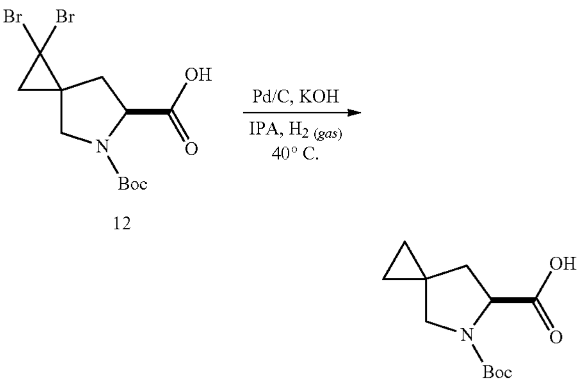

12

4

Reduction to 4

Compound 12 (20.0 g) was dissolved in isopropyl alcohol (160 mL) and then the homogenous mixture was warmed to 40° C. KOH flakes (17.0 g, 6 eq) were added to the solution and it was stirred until the solids were dissolved. The solution was purged with $N_2$ gas and then Pd/C 10% loading Degussa E101 NE/W (4.0 g) was added. The system was re-purged with $H_2$ gas and allowed to stir at 40° C. under 1 atm of $H_2$. Reaction completion was determined by HPLC analysis. Upon completion the solution was cooled to about 22° C. and purged with $N_2$ gas. The solids were removed by filtration through a pad of celite. The solids were rinsed with $H_2O$ (100 mL). The clear solution was then concentrated to half of its original volume. MTBE (60 mL) and 4 M HCl (60 mL) were added to the concentrated solution. The mixture was agitated and then the layers were separated. The aqueous layer was extracted with MTBE (40 mL) and then the organic layers were combined and washed with water (40 mL). The solution was concentrated down to provide 4 as a white solid (9.9 g, 82%).

Variations of reaction conditions and reagents to achieve the hydrogenation are well known to the skilled chemist. For instance, one can use other Pd/C sources, such as palladium hydroxide on carbon. Bases, too, can vary, such as one chosen from potassium carbonate, sodium carbonate, sodium hydroxide, potassium t-butoxide, sodium phosphate, and potassium phosphate.

Suitable alternatives for a solvent include methanol, ethanol, toluene, benzene, and dialkyl ethers and cyclic ethers.

The hydrogenation temperature can range from about 20 to about 80° C.

K. Potassium Salt Formation

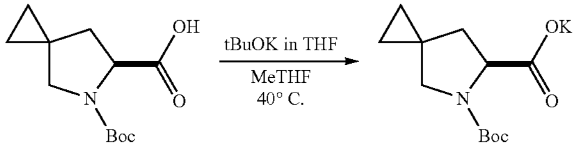

4 10

Potassium Salt Formation to 10

Carboxylic acid 4 (219 g) was dissolved in 2-MeTHF (880 mL) and then the solution was heated to about 35° C. 1.0 M tBuOK solution in THF (1.05 L) was slowly added such that the internal temperature did not exceed 40° C. The slurry was agitated for about 30 minutes and then slowly cooled to about 20° C. over about 2 hours. The slurry was aged at 20° C. for 1 h and then filtered. The cake was washed with 2-MeTHF (715 mL). The solids were dried in a vacuum oven for 24 h at 40° C. The final product 10 was isolated as a white solid (212 g, 86%). $^1$H NMR (400 MHz, $CDCl_3$) δ 4.07 (t, J=7.3 Hz, 1H), 3.44 (d, J=10.4 Hz, 1H), 3.35 (s, 1H), 3.10 (d, J=10.4 Hz, 1H), 2.03 (dd, J=12.3, 6.9 Hz, 1H), 1.89 (dd, J=12.3, 8.0 Hz, 1H), 1.38 (s, 9H), 0.71-0.27 (m, 4H). $^1$H NMR (400 MHz, $d_6$-DMSO, δ): 3.89 (dd, J=8.6, 4.1 Hz, 0.4H rotamer 1), 3.85 (dd, J=8.6, 4.3 Hz, 0.6H rotamer 2), 3.21-3.07 (m, 2H), 2.00-1.92 (m, 1H), 1.75-1.71 (m, 1H) 1.36 (s, 4H rotamer 1), 1.32 (s, 5H rotamer 2), 0.46-0.37 (m, 4H). $^{13}$C NMR (100 MHz, $d_6$-DMSO) δ 174.5, 174.4, 154.1, 153.4, 77.2, 76.9, 62.3, 62.0, 54.1, 53.8, 38.7, 28.4, 28.3, 20.6, 19.9, 11.8, 11.6, 10.5, 10.2.

Other solvents are suitable for salt formation. For instance, these include dialkyl ethers and cyclic ethers.

II. Route to Intermediate 22

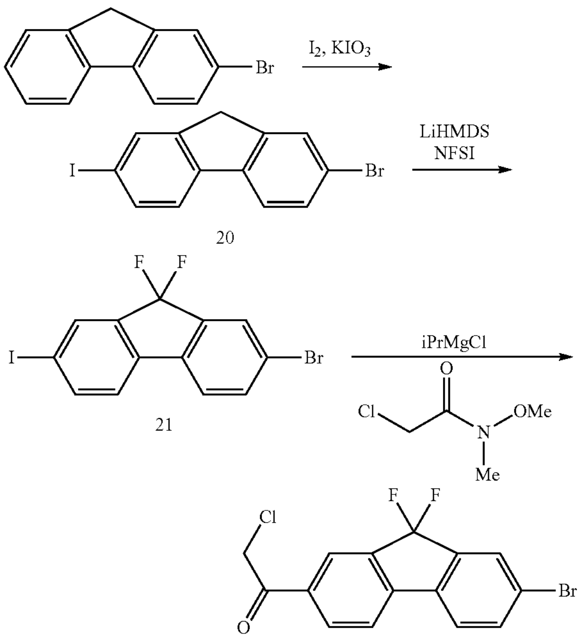

20

21

22

A. Synthesis of Intermediate 20

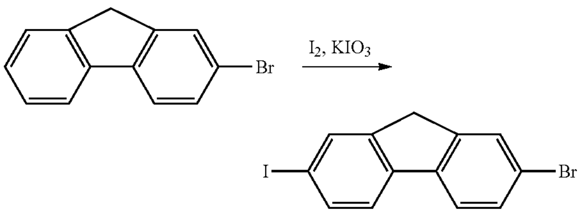

20

A 3-neck flask was charged with 2-bromofluorene (100 g) and acetic acid (2100 g). The contents were heated to 40-45° C. and agitated for approximately 30 minutes to obtain a clear solution. After adjusting the internal temperature to 20-30° C., 20% (v/v) aq. $H_2SO_4$ (200 g, prepared with 64.0 g of $H_2SO_4$ and 136 g of water) was added, followed by $I_2$ (53.0 g, 0.512 mole equiv) followed by $KIO_3$ (17.5 g, 0.200 mole equiv). The slurry was heated at 58° C. (56-60° C.) for about 4 hours. The slurry was then cooled to 20-25° C. and a 9% $Na_2SO_3$ solution ($Na_2SO_3$, 47.0 g; water, 500 g) was charged to the reaction mixture while maintaining the internal temperature at 20-30° C. The slurry was agitated at 25° C. for 1 hour and filtered. The filter cake was rinsed with 85 wt % HOAc (200 g, prepared with 170 g of HOAc and 30 g of water), followed by water (200 g, 2.0 wt equiv). The filter cake was discharged and slurry-washed in water (1500 g) for about 1 hour, then filtered and rinsed with water until pH of the rinse is 6-7, and further rinsed with heptanes (200 g). The solids were dried under vacuum producing 143 g (95% yield, 96% AN purity by HPLC) of the product 20 as a white solid.

Reaction temperatures can range from about 20 to 100° C. Typical temperatures range from about 20 to about 60° C.

B. Synthesis of Intermediate 21

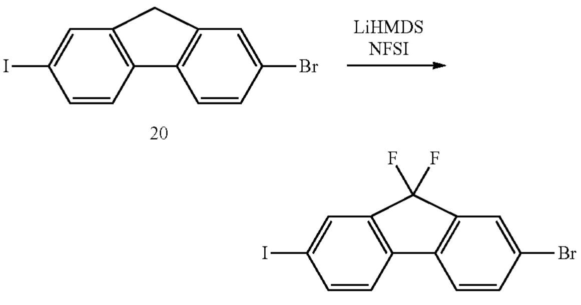

20

21

The starting material (20, 100 g) and N-fluorobenzenesulfonimide (NFSI, 251 g, 2.95 mole equiv) were added as solids to a flask. To the mixture was added THF (1000 g) and with stirring the solids dissolved. The solution was degassed three times by slowly applying vacuum, followed by breaking vacuum with nitrogen. The solution was cooled in a −78° C. bath to an internal temp of −68° C. Upon cooling, a white to off-white slurry was formed. A solution of the base (1.0M LiHMDS in THF, 720 g, 3.00 mole equiv) was added at such a rate that the internal temperature was kept below −55° C. The internal temp was <−60° C. for the majority of the addition, total addition time was about 1 h. The reaction completion was monitored by HPLC analysis. The reaction was quenched by the addition of $NH_3$/MeOH (7N $NH_3$ in MeOH, 8 g) and the cold bath was removed. After the internal temperature had warmed to −20° C., HPLC analysis showed complete consumption of the excess N-fluorobenzenesulfonimide. The internal temperature was adjusted to 0° C. Heptanes (342 g) was added and the solution stirred for 10 minutes. If necessary, the temperature was adjusted to 20-25° C. The slurry was filtered and the solids rinsed with a mixture of THF/heptanes twice (for each rinse: THF, 89.0 g; heptanes: 205 g). The filtrate was stored at 5° C. (2-8° C.) for ca. 20 hours. The solution was then filtered into a flask and concentrated to 2.5-3.0 volumes under vacuum at maximum internal temperature of 35° C. $CH_2Cl_2$ (1500 g) was charged and the slurry agitated at reflux (ca. 40° C.) for 30 minutes. After adjusting the internal temperature to 20-25° C., the slurry was filtered through a pad of celite, and the filter cake was rinsed with DCM (400 g, 4.0 wt equiv). The filtrate was concentrated to about 3.0 volumes under vacuum. Methanol (600 g,) was added and the mixture was concentrated to about 4.0 volumes, additional methanol (300 g) was added and the mixture was concentrated again to about 4.0 volumes (300 volumes). The slurry was filtered and rinsed with methanol twice (for each rinse, 100 g). The product 21 was dried under vacuum producing 90 g (82% yield, 97-98% AN purity by HPLC) of the product as an off-white to pale yellow solid. $^{1}$H NMR (400 MHz, $CDCl_3$, δ): 7.94 (d, J=1.2 Hz, 1H), 7.81 (d, J=7.8 Hz, 1H), 7.74 (d, J=1.4 Hz, 1H), 7.60 (d, J=8.3 Hz, 1H), 7.41 (d, J=8.1 Hz, 1H), 7.29 (d, J=8.0 Hz, 1H). $^{19}$F NMR (376 MHz, $CDCl_3$) δ −111.0 (s, 2F).

In some embodiments, the disclosure provides for the use of other bases for the synthesis of 21. These include, for example, sodium hexamethyldisilazane (NaHMDS), KHMDS, and lithium diisopropylamide (LDA).

C. Synthesis of Intermediate 22

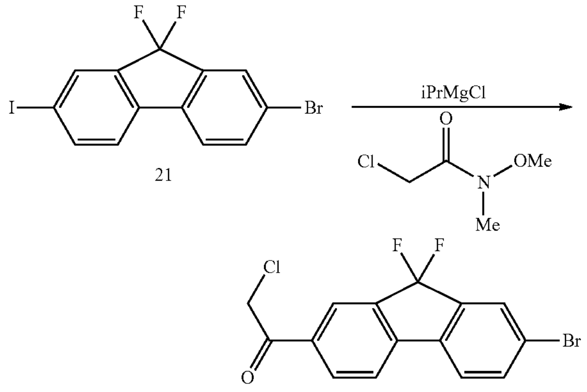

21

22

A 3-neck flask was charged with 21 (100 g) and THF (800 mL). The solution was degassed three times by slowly applying vacuum, followed by breaking vacuum with nitrogen. The solution was cooled to −10° C. internal temperature. A solution of 2N i-PrMgCl solution in THF (125 g, 1.04 mole equiv) was added slowly while maintaining internal temperature at −10° C. to 0° C. The resulting mixture was then stirred for 30 minutes at −10° C. until reaction was complete. 2-Chloro-N-methoxy-N-methylacetamide (40.6 g, 1.20 mole equiv) was dissolved in MTBE (122 g, 1.22 wt equiv) and filtered through a 1 μm filter. The MTBE solution of the acetamide was then added slowly to the flask maintaining internal temperature at −10° C. to 0° C. Upon completion of the addition, the internal temperature was adjusted to 0° C. and agitated for 2 hours. After the reaction is complete, 1N HCl (750 g) was added slowly so that the internal temperature did not exceed 20° C. If necessary, the internal temperature was adjusted to 20° C. The layers were separated and the aqueous layer was extracted with MTBE (410 g). The organic layers were combined and dried over $MgSO_4$. The $MgSO_4$ was filtered off and rinsed with THF (200 g). The filtrate and rinse were concentrated under vacuum 10 volumes (1000 mL). Isopropanol (785 g) was added and small amounts of crystals began to form. This slurry was again concentrated under vacuum to 10 volumes (1000 mL). Isopropanol (785 g) was once again added and the slurry was concentrated under vacuum to 10 volumes (1000 mL). The internal temperature was adjusted to 20-25° C. and agitated for ca. 30 minutes. The slurry was filtered and rinsed with isopropanol (100 g) then dried under vacuum to provide 62.28 g (70.8%, 98% purity by HPLC) of the product 22 as an off-white to pale yellow solid. $^{1}$H NMR (400 MHz, $CDCl_3$, δ): 8.19 (s, 1H), 8.12 (d, J=7.8 Hz, 1H), 7.82 (s, 1H), 7.67 (d, J=8.0 Hz, 2H), 7.52 (d, J=7.8 Hz, 1H), 4.71 (s, 2H). $^{19}$F NMR (376 MHz, $CDCl_3$) δ −111.4 (s, 2F).

In some embodiments, the solvent is 2-MeTHF.

III. Synthesis of Intermediate 24

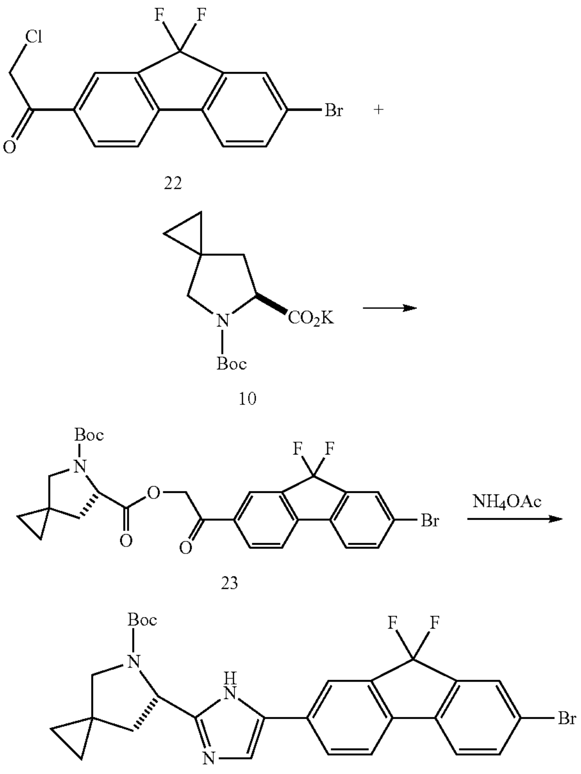

22

10

23

24

A. Preparation of 23

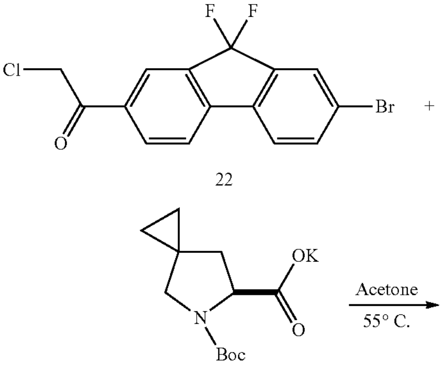

22

10

-continued

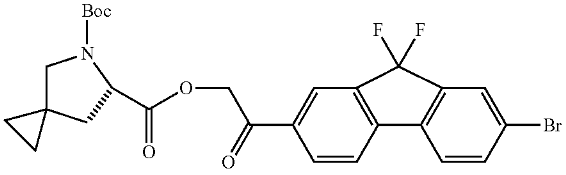

23

Compound 22 (10.8 g, 1.05 eq) and compound 10 (8.0 g, 1.0 eq) were dissolved in acetone (106 mL). The heterogeneous mixture was heated to 55° C. and aged until the reaction was deemed complete as determined by HPLC analysis. Water (22 mL) was added slowly and the solution was held at 55° C. for 30 minutes. The solution was cooled to 50° C. and seed crystals of 23 were added. Another portion of water (11 mL) was slowly added. The solution was aged at 50° C. for 1 h and then cooled to 20° C. (15-25° C.) over a period of 2 hours. The slurry was filtered at 20° C. (15-25° C.) and the filter cake was washed with a mixture of acetone (18 mL) and water (6 mL). The product was dried to afford 23 as a yellow solid (12.8 g, 95%). $^{1}H$ NMR (400 MHz, $CDCl_3$, mixture of rotamers, δ): 8.13 (s, 1H), 8.07-7.97 (m, 1H), 7.79 (s, 1H), 7.67-7.56 (m, 2H), 7.53-7.44 (m, 1H), 5.61 (d, J=16.3 Hz, 0.5H), 5.47 (d, J=16.2 Hz, 0.5H), 5.29 (d, J=16.2 Hz, 0.5H), 5.15 (d, J=16.3 Hz, 0.5H), 4.62 (dd, J=8.7, 3.5 Hz, 0.5H), 4.55 (dd, J=8.7, 4.0 Hz, 0.5H), 3.48-3.28 (m, 2H), 2.43-2.35 (m, 1H), 2.17-2.07 (m, 1H), 1.48 (s, 9H) 0.77-0.55 (m, 4H); $^{13}C$ NMR (100 MHz, $CDCl_3$) δ 190.8, 190.3, 172.2, 172.0, 154.4, 153.7, 143.7-143.4 (m), 140.3 (t, J=25.9 Hz), 138.2 (t, J=25.4 Hz), 136.9-136.5 (m), 135.5, 135.4, 134.7, 134.6, 132.4, 127.7, 124.2, 124.1, 123.2, 123.2, 122.7, 121.6 (t, J=244 Hz), 120.8, 120.8, 80.1, 80.0, 66.0, 65.9, 59.4, 59.0, 54.3, 53.7, 38.9, 38.0, 28.4, 28.3, 20.7, 20.0, 12.9, 12.3, 8.8, 8.3. $^{19}F$ NMR (376 MHz, $CDCl_3$) δ −111.41 (s), −111.43 (s).

In some embodiments, compound 4 is substituted for compound 10. In these embodiments, the synthesis as described above is performed in the presence of a base, such as one chosen from potassium carbonate, sodium carbonate, and tertiary amine bases.

In another embodiment of the reaction shown above, the (1S,2R)-amino-indanol salt of compound 4 (18a) or the 2-aminobutanol salt of compound 4 (compound 18b) is reacted directly with compound 22 to yield compound 23.

In other embodiments, the reaction solvent is an aromatic hydrocarbon, such as toluene or benzene; an aliphatic ether, such as a dialkyl ether, an example of which is diethyl ether; cyclic ethers, such as tetrahydrofuran; alkyl acetates such as ethyl acetate; polar heterocyclic solvents such as N-methylpyrrolidone and 1,3-dimethyl-3,4,5,6-tetrahydro-2-pyrimidinone; and polar aprotic organic solvents such as dimethylformamide and dimethylacetamide.

Suitable reaction temperatures range from about 20 to about 75° C.

B. Imidazole 24 Formation

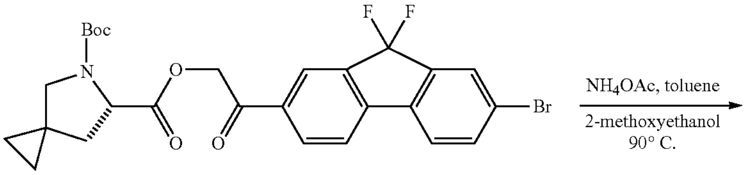

23

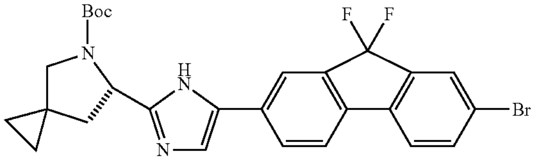

24

To compound 23 (7.0 g) and ammonium acetate (4.8 g, 5.0 eq) were added toluene (62 mL) and 2-methoxyethanol (3.5 mL). The heterogeneous/biphasic mixture was heated to 90° C. and aged until the reaction was deemed complete as determined by HPLC analysis. The solution was cooled to 55° C. and stirred until a slurry of 24 had formed (seeds can be added if necessary). Heptane (104 mL) was charged at 55° C. over 1 h and then the slurry was cooled to 22° C. over 3 h. Once the slurry had reached room temperature it was aged for 1 h. The slurry was filtered and washed with heptane (15 mL). The solids were then dissolved in DMAc (42 mL). The solution was heated to 45° C. and water (7 mL) was charged to the solution. The temperature of the solution was increased to 50° C. and seed crystals of 24 were charged. The slurry was aged for 30 min and then a second portion of water (9.1 mL) was charged over 1 h. Upon completion the slurry was cooled to 22° C. over 3 h and aged at room temperature for 1 h. The solids were filtered and washed with a DMAc (5 mL) and water (2 mL) solution. A final heptane (23 mL) wash was applied to displace the DMAc and water. The solids were dried at 45° C. in a vacuum oven. The final product 24 was isolated as a brown solid (5.2 g, 77%). $^{1}H$ NMR (400 MHz, DMSO, mixture of rotomers, δ): 12.31-11.78 (m, 1H), 8.15-8.03 (m, 1H), 8.02-7.84 (m, 2H), 7.84-7.43 (m, 4H), 5.04-4.84 (m, 1H), 3.62-3.21 (m, 2H), 2.42-2.09 (m, 1H), 2.08-1.78 (m, 1H), 1.40 (s, 4H), 1.17 (s, 5H), 0.75-0.31 (m, 4H); $^{19}F$ NMR (376 MHz, $CDCl_3$) δ −103.85 (s), −104.03 (s).

MS-ESI$^+$: $[M+H]^+$ calcd for $C_{27}H_{27}BrF_2N_3O_2$, 542.1, 544.1; found, 542.1, 544.1.

In some embodiments, imidazole formation is achieved through use of ammonium salts of larger chain carboxylates, $RCO_2^-$, where R is a straight or branched $C_1$-$C_{20}$-alkyl.

In other embodiments, the solvent is selected from toluene, benzene, dialkyl ethers and cyclic ethers, and alkyl acetates such as ethyl acetate. Solvent additives include acetic acid and alcohols (ROH).

Suitable reaction temperatures range from about 50 to about 120° C.

-continued

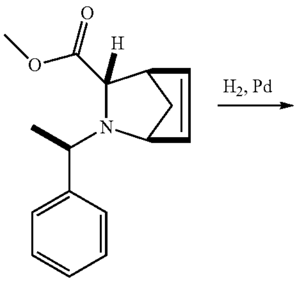

IV. Synthesis of Intermediate 28

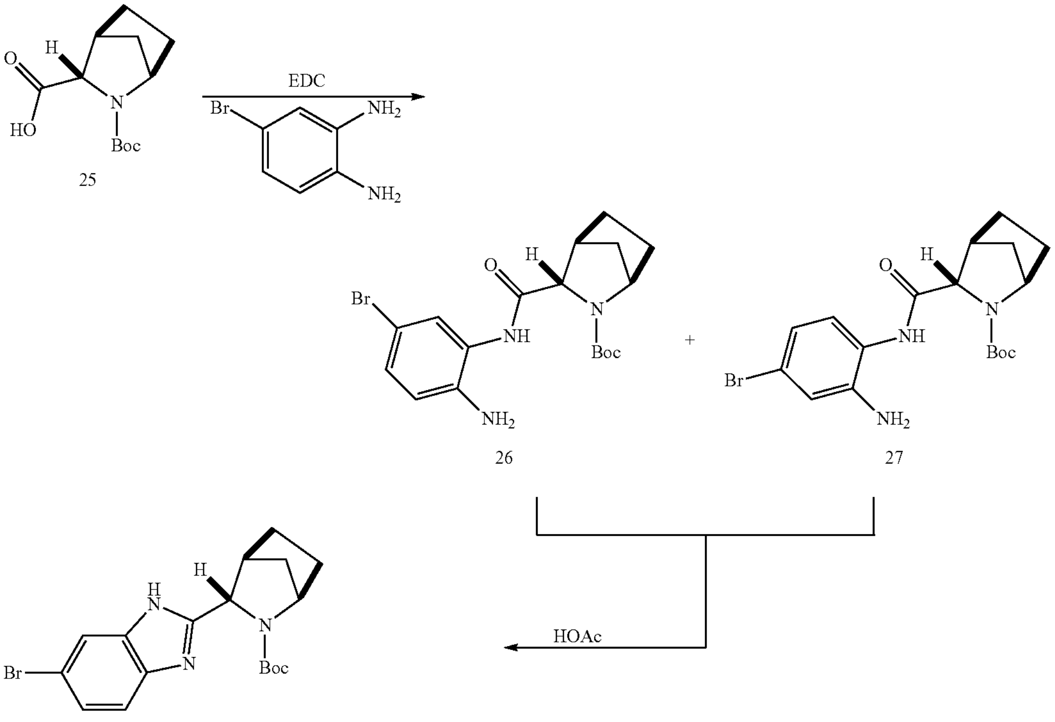

25 26 27 28

A. Synthesis of 25

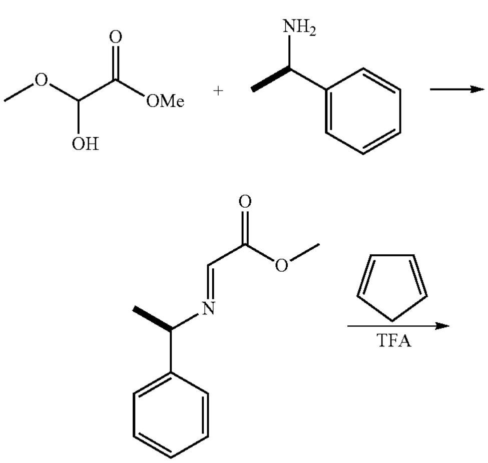

-continued

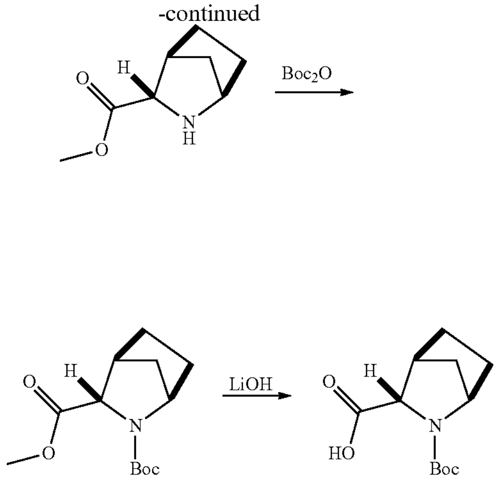

25

B. Synthesis of 26 and 27

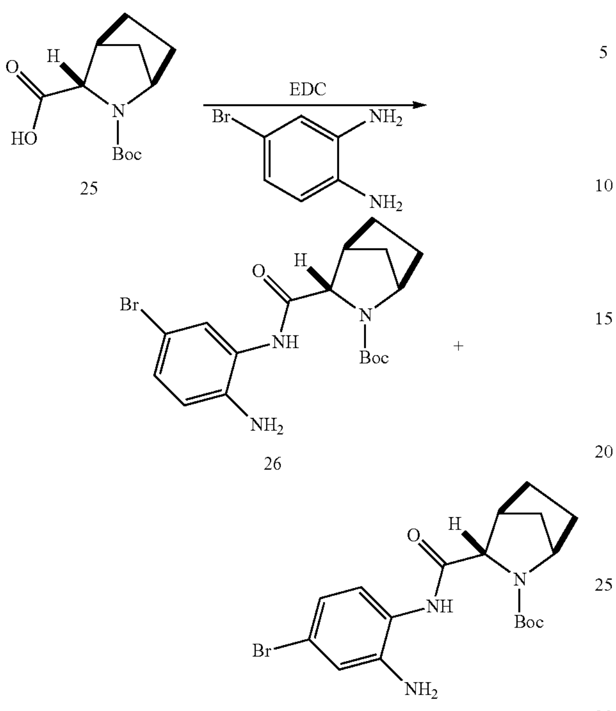

25

26

27

To a flask was charged 25 (20.00 g, 0.083 mol), 4-bromo-1,2-benzenediamine (16.74 g, 0.089 mol, 1.08 equiv.), hydroxybenzotriazole (HOBt) (13.96 g, 0.091 mol, 1.1 equiv.), and 1-ethyl-3-(3-dimethylaminopropyl)carbodiimide HCl (EDC.HCl) (17.48 g, 0.091 mol, 1.1 equiv.). The flask was cooled in an ice bath, and was charged with N,N-dimethylacetamide (DMAC, 80 mL). The reaction was allowed to cool to ca. 10° C. with stirring. N-methylmorpholine (NMM) (27.34 mL, 0.249 mol, 3 equiv.) was added over 5 minutes keeping the internal temperature below 20° C. The reaction was stirred at rt for 20 h. Upon reaction completion, the reaction mixture was added to MTBE (200 mL) and water (600 mL) in a reparatory funnel and was gently shaken. The layers were allowed to separate, and the aqueous layer was removed. The aqueous layer was extracted twice with MTBE (50 mL), and the organic extracts were combined. The combined organic extracts were then extracted with water (500 mL), forming a mixture that did not separate well. The mixture was filtered over an appropriate solid support and the layers were separated. The organic phase was concentrated under vacuum, and the resulting residue was dissolved in diisopropyl ether (100 mL). The solution was cooled to ca. 5° C. with stirring. Acetic acid (5.22 mL, 0.091 mol, 1.1 equiv.) was added slowly keeping the internal temperature below 10° C., and the resulting suspension was stirred 2 h at 5° C. The thick suspension was then filtered, and the solid was rinsed with diisopropyl ether (100 mL), followed by heptane (100 mL). The cake was dried under vacuum to give the product as a light-beige solid as a mixture of regioisomers 26 and 27 (28.19 g, 72%, >99% AN). $^1$H NMR (400 MHz, DMSO) mixture of 26 & 27 (data is for the two rotamers of the major regioisomer): δ 9.25 (s, 0.5H), 9.13 (s, 0.5H), 7.08 (d, J=8.3 Hz, 0.5H); 7.06 (d, J=8.2 Hz, 0.5H), 6.92 (d, J=2.2 Hz, 0.5H), 6.89 (d, J=2.1 Hz, 0.5H), 6.71 (dd, J=8.4, 2.2, 0.5H), 6.66 (dd, J=8.4, 2.2, 0.5H), 5.10 (br s, 1H), 5.05 (br s, 1H), 4.15 (br s, 0.5H), 4.10 (br s, 0.5H), 3.76 (s, 1H), 2.64 (br s, 1H), 1.96-1.88 (m, 1H), 1.77-1.67 (m, 1H), 1.67-1.19 (m, 4H), 1.41 (s, 4.5H), 1.33 (s, 4.5H). MS-ESI$^+$: $[M+H]^+$ calcd for $C_{18}H_{25}BrO_3N_3$, 410.1, 412.1; found, 410.0, 412.0

The disclosure provides in some embodiments the use of other coupling reagents. These include but are not limited to N,N'-dicyclohexylcarbodiimide (DCC), N,N'-diisopropylcarbodiimide (DIC), 6-chloro-2,4-dimethoxy-s-triazine (CDMT), O-benzotriazole-N,N,N',N'-tetramethyl-uronium-hexafluoro-phosphate (HBTU), and 2-(7-Aza-1H-benzotriazole-1-yl)-1,1,3,3-tetramethyluronium hexafluorophosphate (HATU).

The amine base also can be varied or omitted completely. For instance the amine is selected from tertiary amines ($R_3N$), 2,6-lutidine, pyridine, dicyclohexylmethylamine, and N-methylmorpholine (NMM).

Suitable solvent alternatives are selected from DMF, NMP, dialkyl and cyclic ethers $R_2O$, THF, 2-Me-THF, DCM, DCE, toluene, EtOAc, IPAc, Acetone, MIBK, and MEK.

Suitable temperatures for the reaction range from about −20 to 80° C.

C. Synthesis of Intermediate 28

To a reactor was charged the 26/27 mixture (50.0 g, 0.106 mol). MTBE (200 mL, 4V) was charged and to the suspension was added glacial acetic acid (30.4 mL, 0.532 mol, 5 equiv.). The mixture was heated to 55° C. resulting in a brown, homogeneous solution, and was stirred at this temperature for 18 h. Upon reaction completion as determined by HPLC, the solution was cooled to ca. 10° C. and was then quenched with aqueous KOH (35 g in 200 mL $H_2O$) keeping the internal temperature below 20° C. The biphasic mixture was stirred vigorously for 15 min. Agitation was stopped and the layers were allowed to separate. The aqueous layer was drained and back-extracted again with MTBE (50 mL). The organic extracts were combined, $H_2O$ (300 mL) was charged, and the biphasic mixture was stirred vigorously for 15 min. Agitation was stopped and the layers were allowed to separate. The aqueous layer was drained, and the tan organic layer was polish filtered. The solvent was distilled to a volume of ca. 50 mL. Diisopropyl ether (IPE, 150 mL) was added while keeping the internal temperature above 48° C. and the solution was distilled to a total volume of ca. 80 mL. IPE (150 mL) was again added and the solution was distilled to ca. 120 mL. This process was continued until the solvent was mainly diisopropyl ether as indicated by an internal temperature during distillation of about 69° C. or as determined by $^1$H NMR. The total volume was then adjusted to ca. 120 mL, and the solution was allowed to cool slowly (10° C./h) overnight to 0° C. resulting in slurry formation. The slurry was then filtered and rinsed with cold IPE (100 mL). The solids were collected and dried in a vacuum oven to give 28 (39.23 g, 94% yield, >99.5% AN). $^1$H NMR (400 MHz, $CDCl_3$, δ): 10.70 (s, 1H), 7.86 (s, 0.5H), 7.58 (d, J=8.6 Hz, 0.5H), 7.54 (s, 0.5H), 7.30 (d, 8.3 Hz, 1H), 7.25 (d, J=8.0 Hz, 0.5H), 4.52 (d, J=3.6 Hz, 1H), 4.15 (s, 1H), 3.43 (d, J=3.2 Hz, 1H), 2.03-1.94 (m, 1H), 1.93-1.81 (m, 1H), 1.80-1.55 (m, 4H), 1.52 (s, 9H). MS-ESI$^+$: $[M+H]^+$ calcd for $C_{18}H_{23}BrO_2N_3$, 392.1, 394.1; found, 392.1, 393.9

Typical reaction temperatures range from about 20 to 100° C.

In one embodiment, toluene is substituted for IPE and/or MTBE.

V. Synthesis of Compound of Formula I (Compound 31)
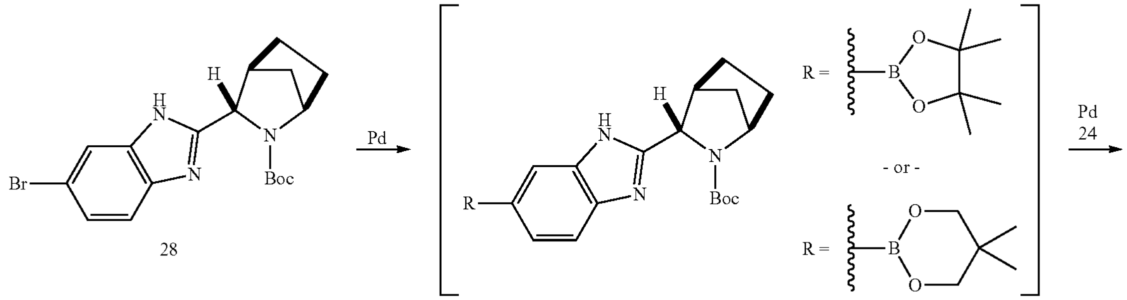
28
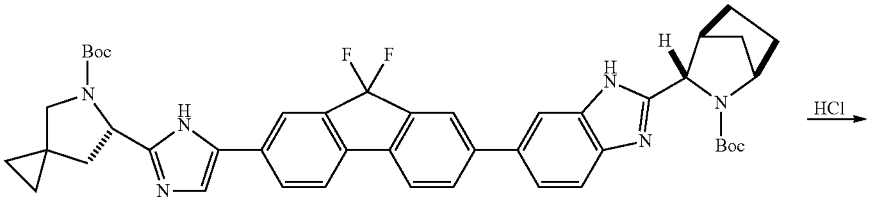
29
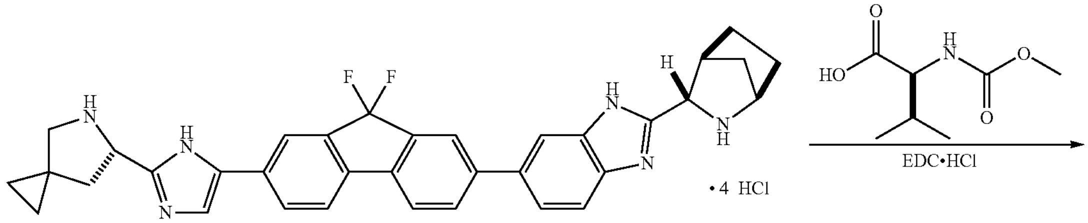
30
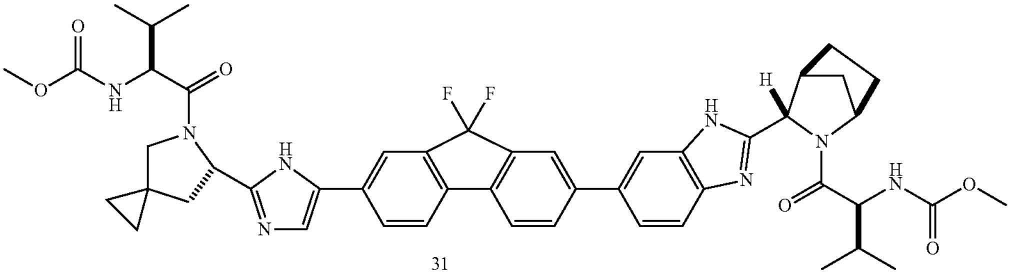
31
31• D-tartrate 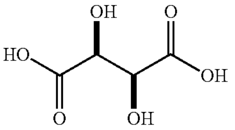
31• acetone solvate 

A. Formation of Compound 29

1a. $PdCl_2[P(t\text{-}Bu)_2Ph]_2$ Example with Bis(pinacolato)diboron

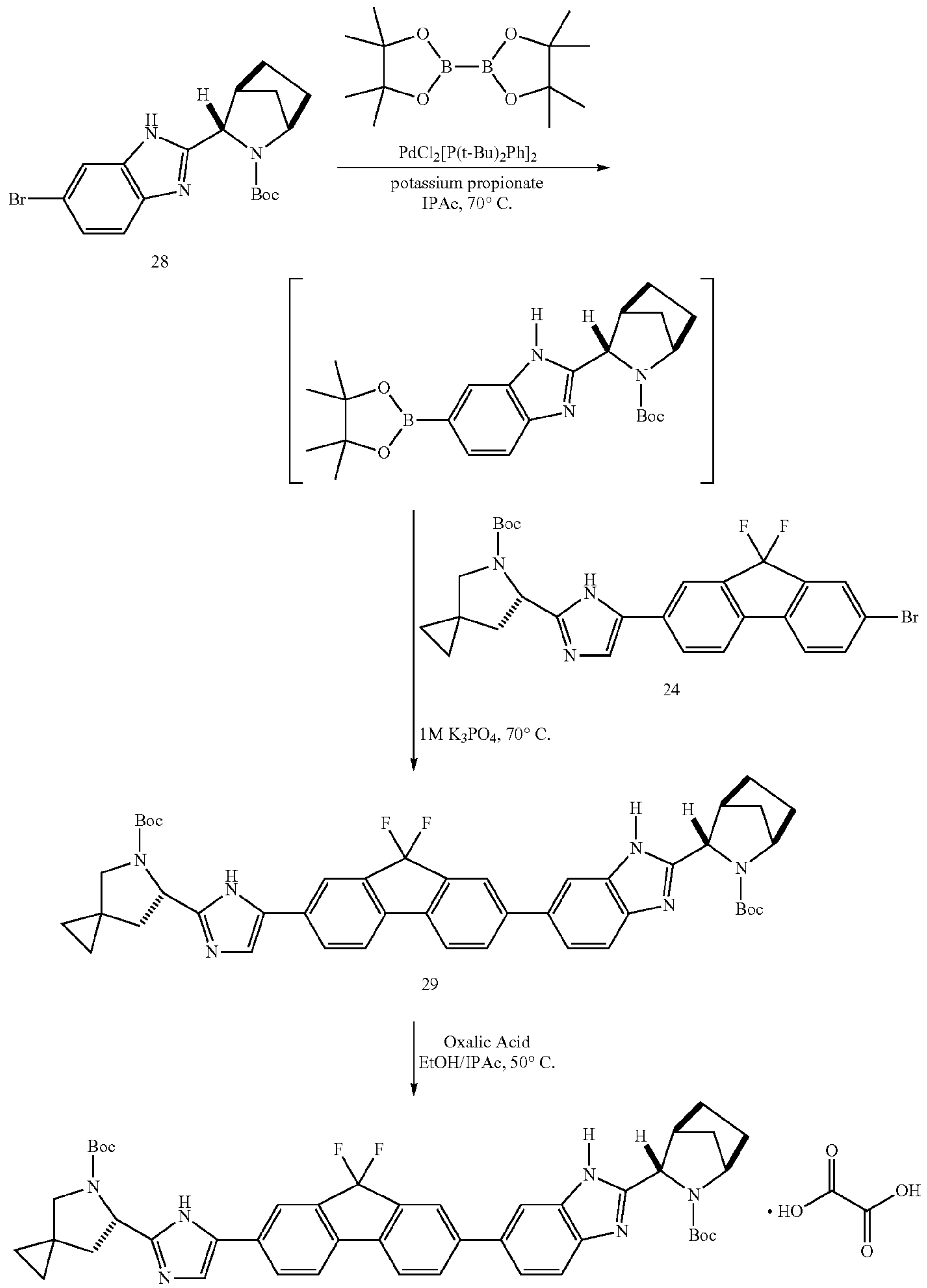

28

24

29

29 oxalate

Compound 28 (24.98 g), bis(pinacolato)diboron (19.40 g), potassium propionate (21.40 g) and $PdCl_2[P(t\text{-}Bu)_2Ph]_2$ (2.04 g) were charged to a reactor, and the reactor was inerted. Isopropyl acetate (250 mL) was charged, stirring was initiated and the reactor was re-inerted. The reaction mixture was heated to 75° C. and agitated for 3.5 h. After cooling to 25° C., compound 24 (29.31 g) was charged to the reaction mixture, and the reactor was inerted. Degassed aqueous 1 M $K_3PO_4$ (223 mL) was charged to the reactor, and the reaction mixture was heated to 75° C. The reaction mixture was held at this temperature for 1 h and was then cooled to 35-40° C. N-Acetyl-L-cysteine (6.27 g) was charged, and the mixture was agitated at 35-40° C. for 15 h. The reaction mixture was cooled to 20° C., agitation was stopped and the layers were allowed to split. The phases were separated and N-acetyl-L- cysteine (6.27 g) was charged to the organic layer. The reaction mixture was heated to 45-50° C. After agitating the mixture at 45-50° C. for 2 h, the reaction was cooled to 20° C. and 5% aqueous NaOH (250 mL) was added. The phases were separated, and the organic layer was washed with 5% aqueous NaCl (125 mL). The organic phase was then treated with 5% aqueous NaCl (125 mL) and transferred to a reparatory funnel via filtration through filter paper. The layers were separated. The organic phase was transferred to a reactor and concentrated to approximately 160 mL by vacuum distillation. iPrOAc (20 mL) was charged to bring the final volume to approx. 180 mL. Ethanol (100 mL) was charged, and the contents were heated to approximately 50° C. A solution of oxalic acid (9.3 g) in ethanol (40 mL) was then charged to the mixture. The solution was seeded with 29 oxalate (200 mg) and aged at 50° C. for 72 h. Isopropyl acetate (240 mL) was charged over 5 h, and the slurry was cooled to 15° C. over 4 h and stirred at this temperature for 20 h. The product was collected by filtration, washed with a solution of ethanol in isopropyl acetate (48 mL EtOH, 191 mL iPrAc) and dried under vacuum at 45° C. to provide 29 oxalate as an off-white solid (41.46 g, 81% yield). $^1H$ NMR (400 MH, DMSO-$d_6$, δ) 11.80 (br s, 4H), 8.11 (d, J=1.2 Hz, 1H), 8.00 (d, J=9.2 Hz, 1H), 7.98 (s, 1H), 7.90 (s, 2H), 7.87, (d, J=9.2 Hz, 1H), 7.85 (s, 1H), 7.80 (s, 1H), 7.60 (dd, J=8.4, 1.2 Hz, 1H), 7.56 (dd, J=7.6, 1.6 Hz, 1H), 5.03 (m, 0.5H), 4.99 (m, 0.5H), 4.52 (s, 0.5H), 4.50 (s, 0.5H), 4.28 (br s, 0.5H), 4.19 (br s, 0.5H), 3.48 (m, 1H), 3.34 (m, 1H), 2.66 (br d, J=12.7 Hz, 1H), 2.38 (m, 0.5H), 2.26 (m, 0.5H), 2.04 (m, 1H), 1.96 (m, 0.5H), 1.86 (d, J=11.6 Hz, 0.5H), 1.77 (m, 1H), 1.70 (m, 1H), 1.64 (2H, m), 1.43 (s, 6H) 1.41 (s, 3H), 1.35 (m, 1H), 1.19 (s, 5H), 1.14 (s, 4H), 0.65 (m, 2H) 0.54 (m, 1H), 0.42 (m, 1H). HRMS-ESI$^+$: $[M+H]^+$ calcd for $C_{45}H_{49}O_4N_6F_2$, 775.3778; found, 775.3773.

1b. $PdCl_2[P(t\text{-}Bu)_2Ph]_2$ Example with Bis(neopentylglycolato)diboron Compound 28 (20.1 g), bis(neopentyl glycolato)diboron (13.2 g), potassium propionate (17.1 g) and $PdCl_2[P(t\text{-}Bu)_2Ph]_2$ (1.6 g) were charged to a reactor, and the reactor was inerted. Isopropyl acetate (200 mL) was charged, stirring was initiated and the reactor was re-inerted. The reaction mixture was heated to 72° C. and agitated for 2 h. After cooling to 20° C., compound 24 (24.9 g) was charged to the reaction mixture, and the reactor was inerted. Degassed aqueous 1 M $K_3PO_4$ (186 mL) was charged to the reactor, and the reaction mixture was heated to 72° C. The reaction mixture was held at this temperature for 1 h and was then cooled to 20° C. The agitation was stopped and the phases were separated. The organic layer was washed with 5% aq. NaCl (300 mL). N-Acetyl-L-cysteine (6 g) was charged, and the mixture was agitated at 20° C. for 16 h. Celite® (5.6 g) was charged then 5% aq. NaOH (100 mL). The mixture was filtered and the phases were separated. N-Acetyl-L-cysteine (6 g) was charged to the organic layer. After agitating the mixture at 20° C. for 12 h, 5% aqueous NaOH (100 mL) was added. The phases were separated, and the organic layer was washed with 5% aqueous NaCl (100 mL). The phases were separated, and the organic layer was washed with another 5% aqueous NaCl (100 mL). The organic phase was transferred to a clean reactor and concentrated to approximately 150 mL by vacuum distillation. Ethanol (101 mL) was charged, and the contents were heated to approximately 50° C. A solution of oxalic acid (4.7 g) in ethanol (34 mL) was then charged to the mixture. The solution was seeded with 29 oxalate (160 mg) and aged at 50° C. for 20 h. Isopropyl acetate (200 mL) was charged over 2 h, the slurry was held for 1 hour, then cooled to 15° C. over 4 h and stirred at this temperature for 20 h. The product was collected by filtration, washed with a solution of ethanol in isopropyl acetate (40 mL EtOH, 162 mL iPrAc) and dried under vacuum at 45° C. to provide 29 oxalate as an off-white solid (33.0 g, 87% yield).

2. $Pd(OAc)_2$/MePhos Example

Compound 28 (69.96 g), bis(pinacolato)diboron (45.33 g), potassium acetate (69.96 g) and MePhos (2-Dicyclohexylphosphino-2'-methylbiphenyl, 6.53 g) were charged to a jacketed reactor, and the vessel was inerted. Freshly degassed t-amyl alcohol (700 mL) was added and stirring was initiated. Palladium acetate (1.99 g) was charged as a solid in one portion, and the reaction mixture was agitated at ambient temperature for 0.5 h, heated to 85° C. and held for 1 h. After cooling to 25° C., compound 24 (82.27 g) and degassed, aqueous $K_3PO_4$ (625 mL, 1.0 M in $H_2O$) were added. The reaction vessel was inerted, and the reaction mixture was heated to 85° C. After stirring at 85° C. for 1 h, the reaction mixture was cooled to 20° C. Following phase separation, the organic layer was washed with 5% aqueous NaCl (2×700 mL) and concentrated in vacuo to provide an oil that was dissolved in isopropyl acetate (1.62 L). Vacuum distillation was continued until a minimum stirrable volume was achieved (ca 300 mL). Additional isopropyl acetate (700 mL) was charged, and the resulting slurry was filtered over celite (28 g). After washing the cake with isopropyl acetate (500 mL), the filtrate was treated with N-acetyl-L-cysteine (17.5 g), and the mixture was agitated for 3.5 h at ambient temperature. The mixture was cooled to 15° C., and 5% aqueous NaOH (700 mL) was charged. After warming to 25° C., the mixture was filtered and the phases were separated. The organic layer was washed with 5% aqueous NaOH (700 mL) and 5% aqueous NaCl (2×700 mL). The resulting organic phase was treated with additional N-acetyl-L-cysteine (17.5 g), and the slurry was agitated for 14 h at ambient temperature. The mixture was cooled to 15° C., and 5% aqueous NaOH was added (700 mL). After warming to 25° C., the phases were separated; and the organic layer was filtered. The filter was washed with isopropyl acetate (160 mL), and the filtrate was washed 5% aqueous NaOH (700 mL) and 5% aqueous NaCl (2×700 mL). The organic phase was filtered and concentrated via vacuum distillation to 500 mL. Additional isopropyl acetate (250 mL) was charged, and the distillation was continued until a final volume of 500 mL was achieved. Ethanol (335 mL) was charged, and the solution was heated to 50° C. A solution of oxalic acid (24.51 g, 136 mmol) in ethanol (110 mL) was charged over 15 min. An ethanol rinse (25 mL) was added. The solution was then seeded with 29 oxalate (527 mg). The slurry was aged at 50° C. for 20 h. Isopropyl acetate (620 mL) was charged over 3 h, and the slurry was cooled to 15° C. over 3 h. The solids were collected by filtration, and the product cake was washed with isopropyl acetate (2×300 mL). After drying, 29 oxalate was isolated as a light yellow solid (117.53 g, 76.9% yield).

In accordance with another embodiment, compound 29 is synthesized in an opposite reaction sequence as shown in the scheme below:

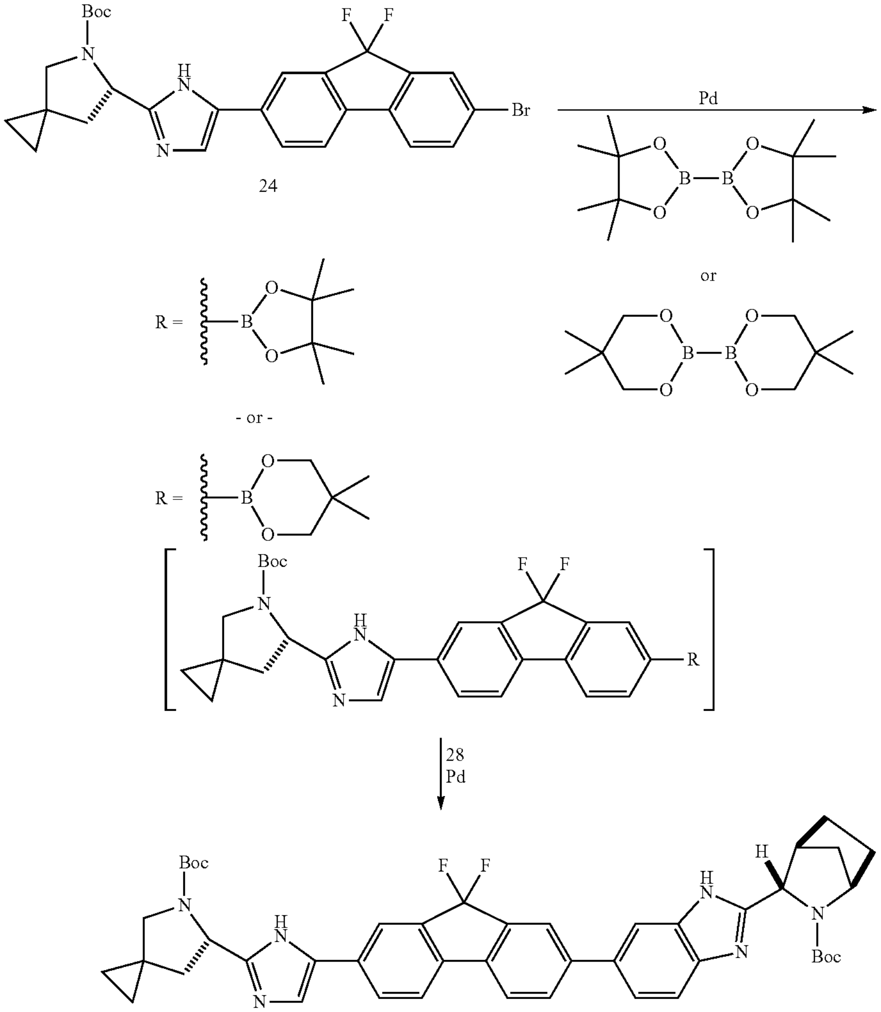
24
29
B. Bis-Boc Deprotection of Compound 29
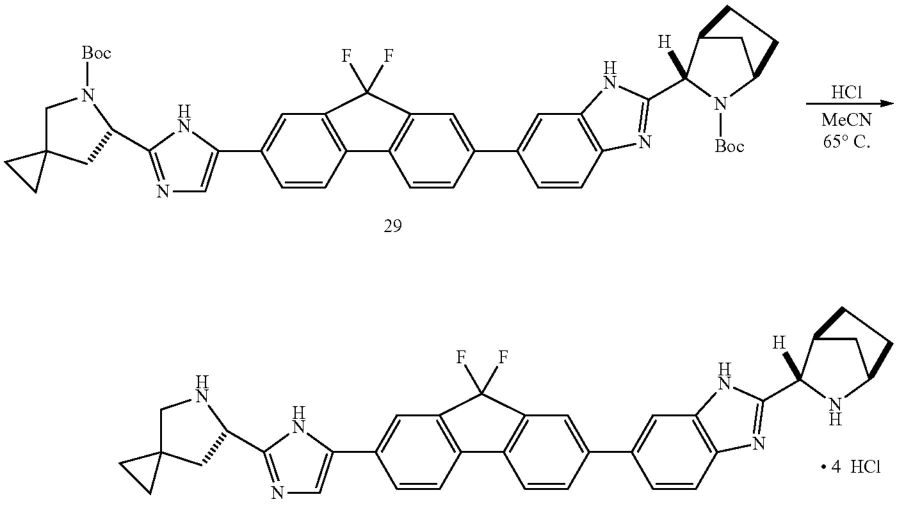
29
30

To a solution of 29 (92.5 g, 119 mmol) in MeCN (324 mL) at 65° C. was charged a 1.5 N aqueous HCl solution (398 mL, 5.0 mol equiv). The reaction mixture was agitated for about 2 h at 65° C. and monitored for completion by HPLC analysis. Upon determination of consumption of starting material, the temperature of the reaction mixture was adjusted to 45° C. Acetonitrile (648 mL) was charged over a course of ≥30 min in order to maintain an internal temperature of 40-50° C. Upon completion of this anti-solvent addition, seed crystals of 30 hydrochloride salt were charged (0.103 g). The slurry was aged at 45° C. for ≥1 h. Additional MeCN (1480 mL) was charged over a course of ≥30 min in order to maintain an internal temperature of 40-50° C. The slurry was cooled to 20° C. over ≥2 h and then filtered. The wet cake was dried to provide 84.6 g of 30 (as its tetra-HCl salt, also including ~6% $H_2O$ content, 80.4% yield). Typical water content ranges from about 4 to about 13%. $^1$H NMR (400 MHz, DMSO-$d_6$, δ): 10.83 (br s, 2H), 10.44 (br s, 2H), 10.33 (br s, 1H), 9.33 (br s, 1H), 8.37 (s, 1H), 8.36 (s, 1H), 8.26 (d, J=8.0 Hz, 1H), 8.08 (d, J=0.8 Hz, 1H), 8.06 (d, J=8.0 Hz, 1H), 8.03 (d, J=0.8 Hz, 1H), 8.01 (d, J=8.4 Hz, 1H), 7.98 (dd, J=8.0, 1.2 Hz, 1H), 7.79 (dd, J=8.4, 0.4 Hz, 1H), 7.75 (dd, J=8.4, 1.2 Hz, 1H), 5.29 (dd, J=8.0, 7.6 Hz, 1H), 4.82 (d, J=3.6 Hz, 1H), 4.19 (s, 1H), 3.65 (d, J=10.8 Hz, 1H), 3.14 (s, 1H), 3.12 (d, J=10.8 Hz, 1H), 2.85 (dd, J=13.2, 9.6 Hz, 1H), 2.23 (dd, J=12.8, 7.6 Hz, 1H), 2.11 (m, 1H), 1.99 (d, J=11.2 Hz, 1H), 1.83 (m, 1H), 1.76 (m, 1H), 1.71 (d, J=10.8 Hz, 1H), 1.67 (m, 1H), 0.84 (m, 2H), 0.70 (m, 2H). HRMS-ESI$^+$: [M+H]$^+$ calcd for $C_{35}H_{33}N_6F_2$, 575.2729; found, 575.2729.

Compound 30 was isolated as a crystalline solid from a mixture of $CH_3CN$ and aq. HCl. In one embodiment, compound 30 is a crystalline polymorph, Form I, that was characterized by X-ray powder diffraction (XRPD). The X-ray powder diffractogram is shown in FIG. 1.

In one embodiment, Form I is characterized by XRPD peaks comprising 7.1, 8.2, 10.8° 2θ±0.2° 2θ as obtained on a diffractometer at 25° C. using Cu—K$_\alpha$ radiation at 1.54060 Å.

In another embodiment, Form I is characterized by XRPD peaks comprising 7.1, 8.2, 10.8, 11.1, 12.8, 14.1, 14.8, 16.1, 18.9, 24.5, 24.9, and 25.9° 2θ±0.2° 2θ.

Figure 2:
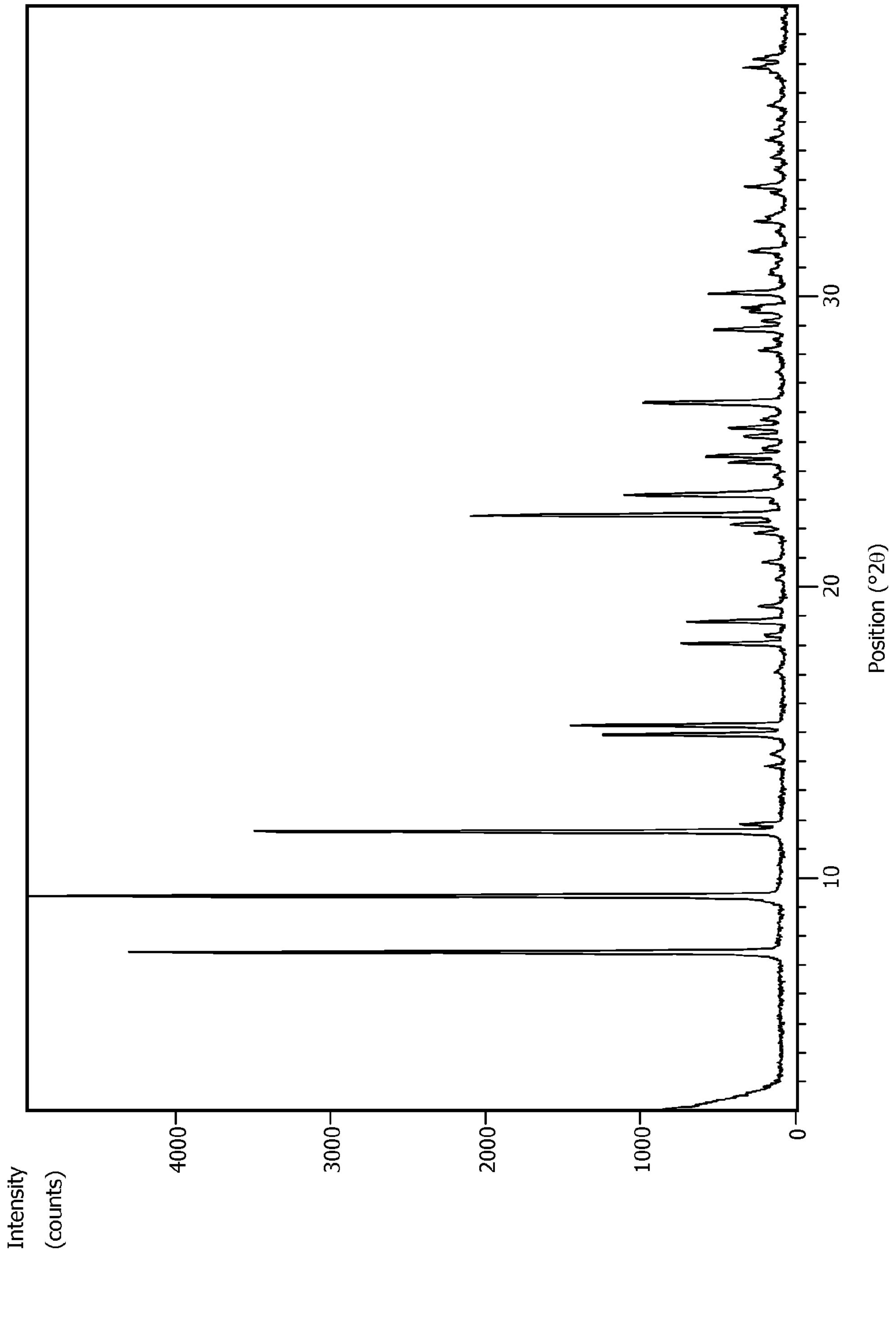
FIG. 2 is an X-ray powder diffractogram of Form II, a crystalline polymorph of compound 30 as described hereinbelow.

In one embodiment, compound 30 is a crystalline polymorph, Form II, that was characterized by X-ray powder diffraction (XRPD). The X-ray powder diffractogram is shown in FIG. 2.

In one embodiment, Form II is characterized by XRPD peaks comprising 7.4, 9.4, 11.6° 2θ±0.2° 2θ as obtained on a diffractometer at 25° C. using Cu—K$_\alpha$ radiation at 1.54060 Å.

In another embodiment, Form II is characterized by XRPD peaks comprising 7.4, 7.5, 9.4, 11.6, 14.9, 15.2, 22.5, 23.2, and 26.3° 2θ±0.2° 2θ.

In accordance with other embodiments, deprotection can proceed by use of other reagents. These include, without limitation, HCl, HBr, phosphoric acid, p-toluenesulfonic acid, sulfuric acid, benzenesulfonic acid, and TFA.

Suitable solvent alternatives include alcohols such as isopropyl alcohol, ethanol. and n-butanol; polar aprotic organic solvents such as N,N-dimethylacetamide; polar heterocyclic solvents such as N-methylpyrrolidone; cyclic ethers, such as tetrahydrofuran and 2-methyl tetrahydrofuran; aliphatic ethers such as diethyl ether and diisopropyl ether; alkyl acetates such as ethyl acetate and isopropyl acetate; and aromatic hydrocarbons such as benzene and toluene.

Typical reaction temperatures range from about 20 to about 85° C.

C. Amide Coupling

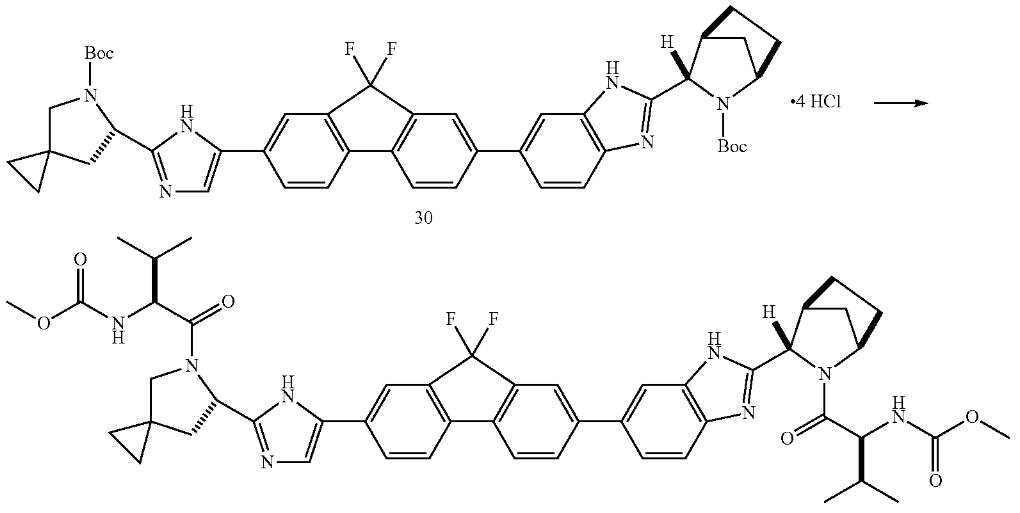

EDC-HCl (4.39 g), HOBt (2.06 g), Moc-Valine (4.02 g), and DMF (50 mL) were charged to a flask. The reaction mixture was agitated for 20 min at 23° C. The solution was then cooled to 0° C. 30-HCl salt (5.0 g) and N-methylmorpholine (5.03 mL) were charged to the reaction mixture. The contents were warmed to room temperature and stirred for 4 hours at 23° C. Water (2.5 mL) was added to the reaction mixture and the contents were stirred for 15 hours at 23° C. EtOAc (70 mL) and water (100 mL) were added and the layers were separated. To the organic layer was added EtOAc (50 mL) and water (50 mL), the layers mixed and then separated. The organic layer was washed with 5% NaHCO$_3$ (50 mL) and water (2×25 mL). The organic layer was then distilled to 2.5 vols (12.5 mL) and cooled to 23° C. Acetone (70 mL) was added to the organic layer. The reaction contents were seeded with compound 31 (acetone solvate) and stirred for 15 hours. The contents were filtered, the wet cake was washed with acetone (5 mL) and the cake was dried to provide 4.78 g of 31 as the acetone solvate (73%). $^1$H NMR (400 MHz, DMSO-$d_6$, δ): 12.29 (s, 0.1H), 12.19 (d, J=4.0 Hz, 1H), 12.14 (s, 0.2H), 11.85 (s, 1H), 8.10 (s, 0.1H), 8.08 (s, 1H), 8.01 (s, 0.1H), 7.963 (m, 1H), 7.955 (s, 1H), 7.89 (d, J=6.4 Hz, 1H), 7.87 (s, 1H), 7.83 (dd, J=8.4, 2.4 Hz, 1H), 7.79 (dd, J=7.2, 2.8 Hz, 1H), 7.78-7.90 (misc., 0.9H), 7.70 (s, 1H), 7.61 (d, J=8.4 Hz, 1H), 7.55 (s, 1H), 7.51 (dd, J=8.8, 1.6 Hz, 1H), 7.44 (m, 0.1H), 7.31 (d, J=8.4 Hz, 1H), 7.21 (d, J=8.4 Hz, 1H), 6.91 (d, J=8.0 Hz, 0.2H), 6.77 (m, 0.2H), 5.34 (d, J=7.6 Hz, 0.1H), 5.20 (dd, J=8.0, 5.2 Hz, 1H), 5.18 (m, 0.1H), 4.88 (s, 0.1H), 4.67 (d, J=6.4 Hz, 1H), 4.55 (s, 1H), 4.17 (dd, J=8.0, 8.0 Hz, 1H), 4.10 (m, 0.2H), 4.01 (dd, J=8.4, 8.0 Hz, 1H), 3.97 (m, 0.1H), 3.82 (d, J=9.6 Hz, 1H), 3.77 (s, 0.2H), 3.71 (d, J=9.6 Hz, 1H), 3.554 (s, 3H), 3.548 (s, 3H), 3.43 (s, 0.4H), 3.20 (d, J=7.6 Hz, 0.3H), 2.77 (s, 0.1H), 2.66 (s, 1H), 2.41 (d, J=8.8 Hz, 1H), 2.22 (dd, J=12.4, 8.0 Hz, 1H), 2.13 (m, 0.4H), 2.08 (s, 6H), 2.05 (dd, J=13.2, 5.2 Hz, 1H), 1.99 (m, 2H), 1.92 (m, 1H), 1.77 (m, 2H), 1.61 (m, 0.3H), 1.56 (m, 1H), 1.46 (d, J=9.2 Hz, 1H), 1.33 (d, J=10.0 Hz, 0.1H), 0.97 (dd, J=6.4, 2.0 Hz, 3H), 0.93 (d, J=6.8 Hz, 3H), 0.88 (d, J=6.4 Hz, 3H), 0.87 (d, J=6.4 Hz, 3H), 0.80-1.05 (misc., 2H), 0.70 (m, 1H), 0.59 (m, 2H), 0.54 (m, 1H), 0.33 (m, 0.1H). HRMS-ESI$^+$: $[M+H]^+$ calcd for $C_{49}H_{55}O_6N_8F_2$, 889.4207; found, 889.4205.

In some embodiments, the coupling agent is one selected from DCC, DIC, CDMT, HBTU, and HATU.

Suitable bases, according to other embodiments, include tertiary amines $R_3N$, 2,6-lutidine, pyridine, dicyclohexylmethylamine, and NMM.

Alternative solvents useful for the coupling described above include DMAc, ACN, EtOAc, isopropyl acetate (IPAc), MeTHF, IPA, and t-BuOH.

Typical coupling reaction temperatures range from about −30 to about 50° C.

Tartrate Salt Formation

Compound 31 (as the acetone solvate, 4.8 g) was added to a flask followed by EtOAc (36 mL) and heated to 50° C. D-Tartaric acid (816 mg) in EtOH (35 mL) was then added. The solution was seeded with 31.D-tartaric acid crystals and stirred at 50° C. for 16 hours. The solution was cooled to 23° C. over 3 hours then filtered. The wet cake was rinsed with 1:1 solution of EtOAc:EtOH (9 mL) and the solids were dried to provide 4.33 g (82%) of 31 as the D-tartrate salt. $^1$H NMR (400 MHz, DMSO-$d_6$, δ): 12.2 (br s, 2H), 8.08 (s, 1H), 7.97 (s, 1H), 7.95 (d, J=8.4, 1H), 7.89 (d, J=8.4, 1H), 7.88 (s, 1H), 7.85 (d, J=8.4, 1H), 7.82 (d, J=8.0, 1H), 7.68 (s, 1H), 7.58 (d, J=8.4, 1H), 7.53 (d, J=8.4, 1H), 7.30 (d, J=8.8, 1H), 7.20 (d, J=8.4, 1H), 5.21 (dd, J=8.0, 5.2, 1H), 4.67 (s, 1H), 4.55 (s, 1H), 4.33 (s, 2H), 4.17 (dd, J=8.0, 8.4, 1H), 4.01 (dd, J=8.0, 8.4, 1H), 3.82 (d, J=10.0, 1H), 3.72 (d, J=9.6, 1H), 3.55 (s, 3H), 2.67 (s, 1H), 2.41 (d, J=9.2, 1H), 2.21 (dd, J=12.4, 8.0, 1H), 2.05 (dd, J=12.4, 5.2, 1H), 1.98 (m, 2H), 1.92 (m, 1H), 1.77 (m, 2H), 1.56 (m, 1H), 1.46 (d, J=9.2, 1H), 0.97 (d, J=6.8, 3H), 0.93 (d, J=6.4, 3H), 0.88 (d, J=6.4, 3H), 0.86 (d, J=6.4, 3H), 0.70 (m, 1H), 0.54 (m, 1H), 0.55-0.62 (m, 2H). HRMS-ESI$^+$: $[M+H]^+$ calcd for $C_{49}H_{55}O_6N_8F_2$, 889.4207; found, 889.4229.

In another embodiment, the tartrate salt is formed from compound 31 in its solvent-free form.

We claim:

1. A process for making a compound of formula I:

(I)

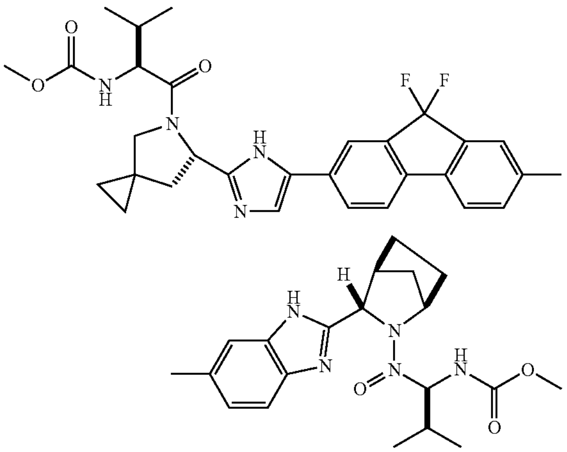

or a pharmaceutically acceptable salt thereof, comprising (A) coupling a compound of formula (i)

(i)

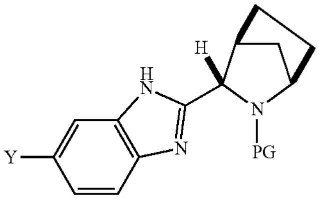

with a compound of formula (ii)

(ii)

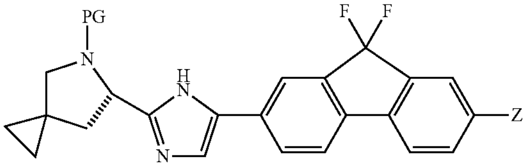

in the presence of a metal catalyst which is $PdCl_2[P(t-Bu)_2Ph]_2$ or $Pd(OAc)_2$/2-dicyclohexylphosphino-2'-methylbiphenyl, and base to yield a compound of formula (iii) or a salt thereof:

(iii)

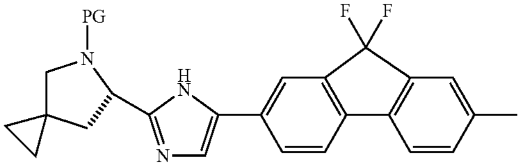

-continued

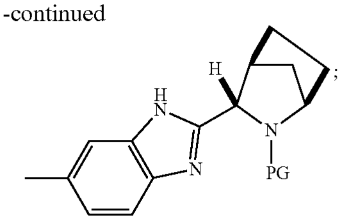

(B) deprotecting a compound of formula (iii) to yield a compound of formula (iv):

(iv)

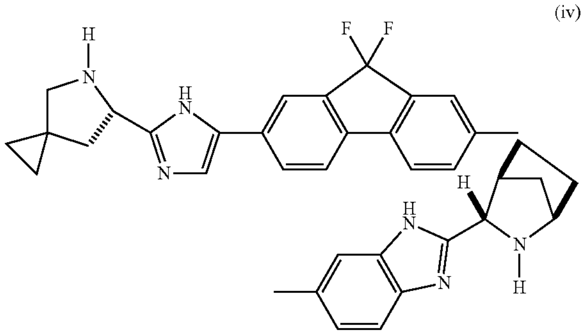

or a salt thereof;

(C) contacting the compound of formula (iv) with (5)-2-(methoxycarbonylamino)-3-methylbutanoic acid:

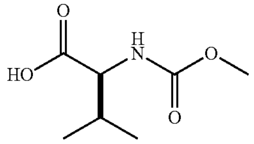

to yield a compound of formula I; wherein each PG independently is an amine protecting group;

Y is —B(OR)(OR') and Z is Br; and

R and R' are independently selected from the group consisting of hydrogen and straight or branched $C_{1-8}$-alkyl, or R and R' together represent a straight or branched $C_{1-8}$-alkylene, $C_{3-8}$-cycloalkylene, or $C_{6-12}$-arylene, wherein any alkyl, alkylene, cycloalkylene, or arylene is optionally substituted with one or more substituents selected from the group consisting of $C_{1-6}$-alkyl, —C(O)N($C_{1-6}$-alkyl$)_2$, and —C(O)O($C_{1-6}$-alkyl).

2. The process according to claim 1, further comprising the step of in situ generation of the compound of formula (i), (i)

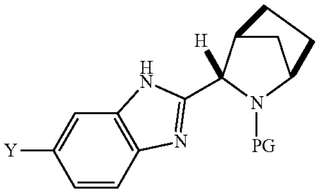

comprising sequentially contacting a compound of formula (a)

(a)

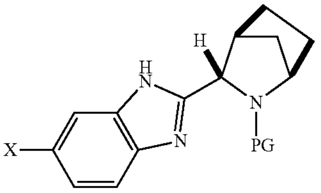

with a source of palladium and then a borylation agent comprising the moiety

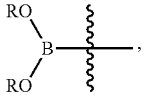

in the presence of a second base, whereby the compound of formula (i) is formed in situ, and X is a halide selected from Cl, Br, and I.

3. The process according to claim 2, wherein the step of in situ generation of the compound of formula (i) and step (A) are carried out sequentially in one pot.

4. The process according to claim 2, where the borylation agent is selected from bis(pinacolato)diboron and bis(neopentylglycolato)diboron.

5. The process according to claim 4, where the borylation agent is bis(pinacolato)diboron.

6. The process according to claim 4, where the borylation agent is bis(neopentylglycolato)diboron.

7. The process according to claim 3, wherein X is Br and PG is tert-butoxycarbonyl.

8. The process according to claim 1, wherein the metal catalyst is $PdCl_2[P(t\text{-}Bu)_2Ph]_2$.

9. The process according to claim 1, wherein the metal catalyst is $Pd(OAc)_2$/2-dicyclohexylphosphino-2'-methylbiphenyl.

10. The process according to claim 2, wherein the second base is a propionate salt.

11. The process according to claim 10, wherein the propionate salt is potassium propionate.

12. A process for making a compound of formula I:

(I)

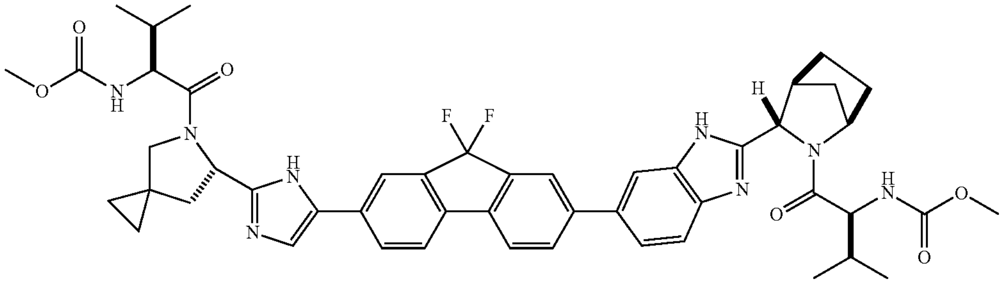

or a pharmaceutically acceptable salt thereof, comprising (1) sequentially contacting a compound of formula (a')

(a')

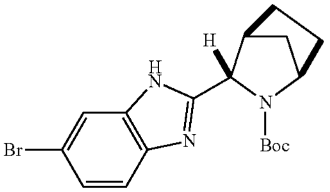

with a catalytically effective amount of $PdCl_2[P(t-Bu)_2Ph]_2$ and bis(neopentylglycolato)diboron in the presence of potassium propionate to yield a reaction mixture comprising a compound of formula (ia):

(ia)

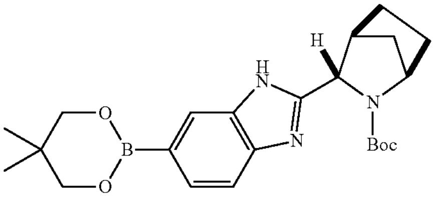

;

(2) contacting the reaction mixture from step (1) with a compound of formula (ii'):

(ii')

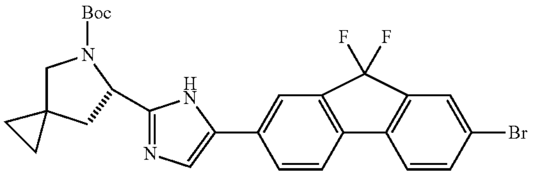

and potassium phosphate to yield a compound of formula (iii'):

(iii')

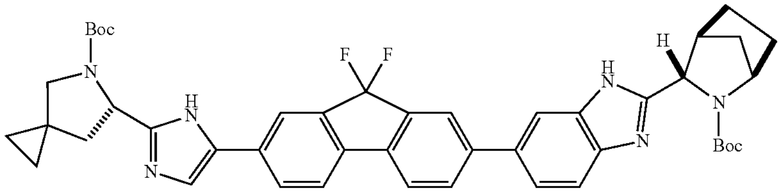

and optionally contacting the compound of formula (iii') with oxalic acid to yield an oxalate salt of formula (iii"):

(iii")

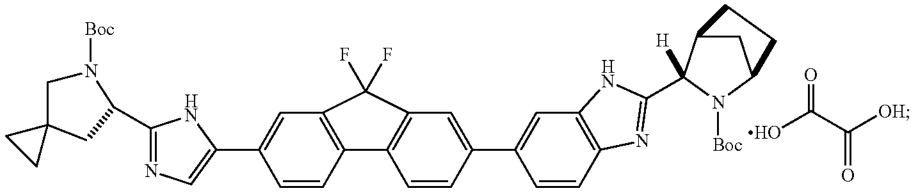

;

(3) contacting the compound of formula (iii') or formula (iii") with HCl to yield a compound of formula (iv'):

(iv')

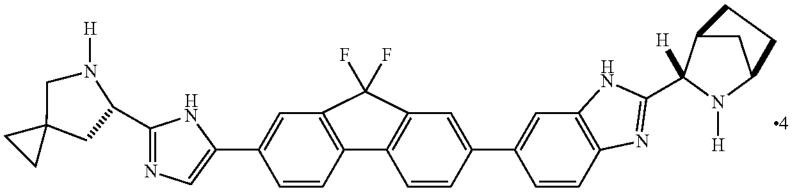

•4 HCl;

(4) contacting the compound of formula (iv') with (S)-2-(methoxycarbonylamino)-3-methylbutanoic acid:

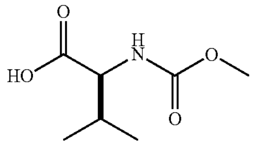

to yield a compound of formula I;

wherein Boc in each instance represents tert-butoxycarbonyl.

13. A process for making a compound of formula I:

(ib)

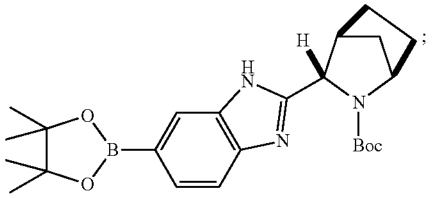

(2) contacting the reaction mixture from step (1) with a compound of formula (ii'):

(I)

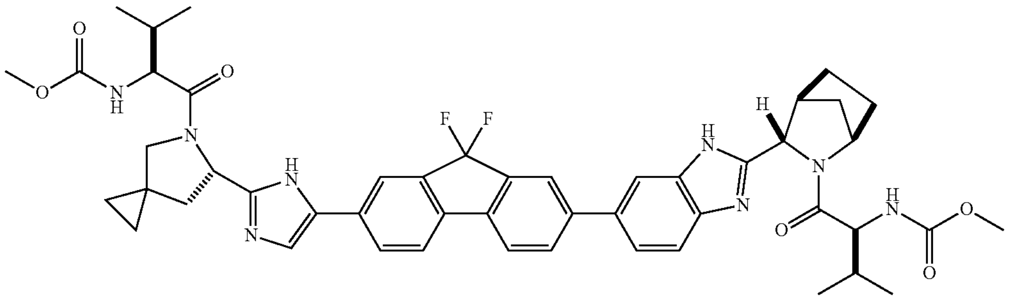

or a pharmaceutically acceptable salt or solvate thereof, comprising (1) sequentially contacting a compound of formula (a')

(a')

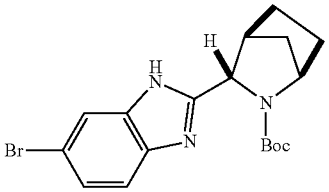

with a catalytically effective amount of $PdCl_2[P(t\text{-}Bu)_2Ph]_2$ and bis(pinacolato)diboron in the presence of potassium propionate to yield a reaction mixture comprising a compound of formula (ib):

(ii')

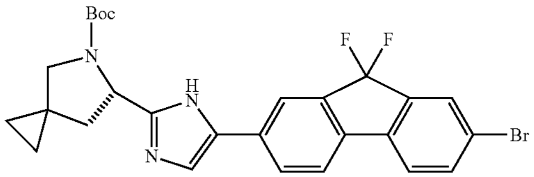

and potassium phosphate to yield a compound of formula (iii'):

(iii')

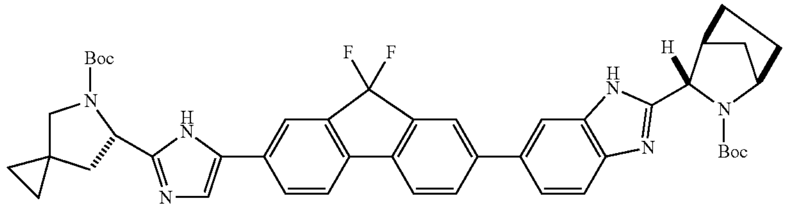

and optionally contacting the compound of formula (iii') with oxalic acid to yield an oxalate salt of formula (iii"):

(iii″)
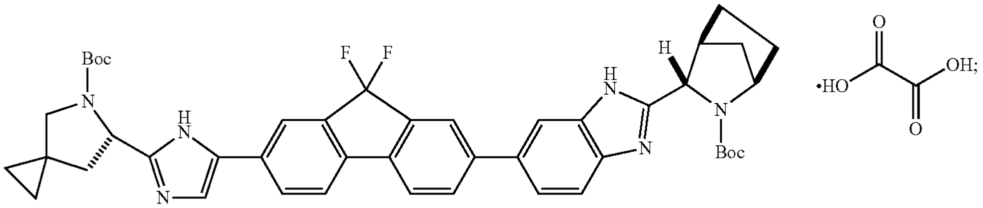
(3) contacting the compound of formula (iii') or formula (iii") with HCl to yield a compound of formula (iv'):
(iv')
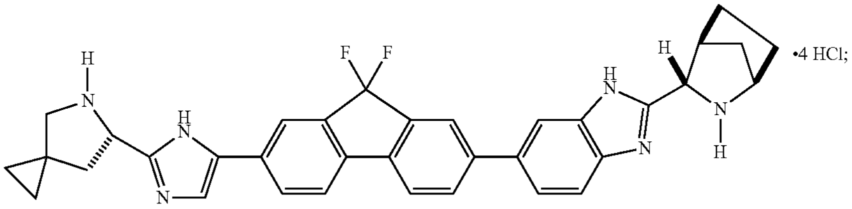
(4) contacting the compound of formula (iv') with (S)-2-(methoxycarbonylamino)-3-methylbutanoic acid:
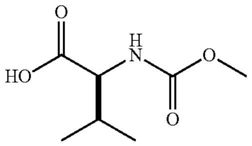
to yield a compound of formula I;
wherein Boc in each instance represents tert-butoxycarbonyl.
* * * * *